(12) United States Patent
Ohlfest et al.

(10) Patent No.: US 10,206,986 B2
(45) Date of Patent: Feb. 19, 2019

(54) ANNEXIN II VARIANT COMPOSITIONS AND METHODS

(71) Applicant: REGENTS OF THE UNIVERSITY OF MINNESOTA, Minneapolis, MN (US)

(72) Inventors: John R. Ohlfest, Minneapolis, MN (US); Michael R. Olin, Spring Park, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/036,115

(22) PCT Filed: Nov. 13, 2014

(86) PCT No.: PCT/US2014/065390
§ 371 (c)(1),
(2) Date: May 12, 2016

(87) PCT Pub. No.: WO2015/073632
PCT Pub. Date: May 21, 2015

(65) Prior Publication Data
US 2016/0279212 A1      Sep. 29, 2016

Related U.S. Application Data

(60) Provisional application No. 61/903,628, filed on Nov. 13, 2013.

(51) Int. Cl.
| | |
|---|---|
| *A61K 39/00* | (2006.01) |
| *A61K 39/39* | (2006.01) |
| *A61K 38/17* | (2006.01) |
| *A61K 35/35* | (2015.01) |
| *A61K 35/15* | (2015.01) |

(52) U.S. Cl.
CPC .......... *A61K 39/0011* (2013.01); *A61K 35/15* (2013.01); *A61K 38/1709* (2013.01); *A61K 39/39* (2013.01); *A61K 2039/5154* (2013.01); *A61K 2039/5158* (2013.01); *A61K 2039/55516* (2013.01); *A61K 2039/572* (2013.01); *A61K 2039/6031* (2013.01); *A61K 2039/6081* (2013.01); *C07K 2319/00* (2013.01)

(58) Field of Classification Search
CPC ................ A61K 35/15; A61K 38/1709; A61K 39/0011; A61K 39/39; A61K 2039/55516; A61K 2039/5154; A61K 2039/5158; A61K 2039/572; A61K 2039/6031; A61K 2039/6081; C07K 2319/00
See application file for complete search history.

(56) References Cited

U.S. PATENT DOCUMENTS

| | | |
|---|---|---|
| 7,666,984 B2 | 2/2010 | Weinschenk et al. |
| 7,695,725 B2 | 4/2010 | Dubensky, Jr. et al. |
| 9,555,074 B2 | 1/2017 | Ohlfest et al. |
| 2004/0096467 A1 | 5/2004 | Kalden et al. |
| 2011/0293608 A1 | 12/2011 | Jaffee et al. |

FOREIGN PATENT DOCUMENTS

| | | |
|---|---|---|
| KR | 20100125079 A | 11/2010 |
| WO | WO 2001/011372 A1 | 2/2001 |
| WO | WO 2002/017857 A2 | 3/2002 |
| WO | WO 2012/048190 A1 | 4/2012 |

OTHER PUBLICATIONS

U.S. Appl. No. 15/390,948, filed Dec. 27, 2016, Ohlfest et al.
International Search Report and Written Opinion for PCT/US2014/065390, issued by the European Patent Office, Mar. 30, 2015; 12 pgs.
International Preliminary Report on Patentability for PCT/US2014/065390, issued by the International Bureau of WIPO, May 26, 2016; 9 pgs.
AZK35814, "Human annexin A2 peptide, SEQ ID 31 #2" retrieved from EBI Accession No. GSP: AZK35814, Sep. 1, 2011; 1 pg.
AZK35688, "Human annexin A2 peptide, SEQ ID 34 #1" retrieved from EPI Accession No. GSP: AZK35688, Sep. 1, 2011; 1 pg.
Apetoh et al., "Toll-like receptor 4-dependent contribution of the immune system to anticancer chemotherapy and radiotherapy," *Nature Medicine*, 2007; 13:1050-1059.
Borthwick et al., "The formation of the cAMP/Protein Kinase A-dependent annexin 2-S1OOA1O complex with cystic fibrosis conductance regulator protein (CFTR) regulates CFTR channel function," *Molecular Biology of the Cell*, 2007;18:3388-3397.
Frances et al. "Extreme skewing of annexin Ii and S1OOA6 expression identified by proteomic analysis of peritoneal B-1 cells," *International Immunology*, 2006;19(1):59-65.
Ko et al., "Sunitinib Mediates Reversal of Myeloid-Derived Suppressor Cell Accumulation in Renal Cell Carcinoma Patients," *Clinical Cancer Research*, 2009;15:2148-2157.
Li et al., "LEC/chTNT-3 Fusion Protein for the Immunotherapy of Experimental Solid Tumors," *J Immunother*, Jul./Aug. 2003;26(4):320-331.
Löscher et al., "Drug resistance in brain diseases and the role of drug efflux transporters," *Nature Reviews Neuroscience*, Aug. 2005; 6:591-602.
Ohlfest, "Overcoming Barriers to Effective Immune and Drug Therapies for Brain Diseases," presented on Jun. 21, 2010; 73 pgs.
Richardson, "Molecular Mechanisms of Iron Uptake by Cells and the Use of Iron Chelators for the Treatment of Cancer," 2005; 12(23):2711-2729.
Stupp et al., "Radiotherapy plus Concomitant and Adjuvant Temozolomide for Glioblastoma," *The New England Journal of Medicine*, Mar. 2005; 352:987-996.
Swisher et al., "Annexin A2 tetramer activates human and murine macrophages through TLR4," *Blood*, Jan. 2010;115(3):549-558.
Tatiana et al., "BLAST 2 Sequences a new tool for comparing protein and nucleotide sequences," *FEMS Microbiol Lett*, May 1999;174(2):247-250.
Wu et al., "In Vivo Vaccination With Tumor Cell Lysate Plus CpG Oligodeoxynucleotides Eradicates Murine Glioblastoma," *J. Immunotherapy*, 2007;30(8): 789-797.

*Primary Examiner* — Robert S Landsman
*Assistant Examiner* — Bruce D. Hissong
(74) *Attorney, Agent, or Firm* — Mueting, Raasch & Gebhardt, PA

(57) ABSTRACT

This disclosure describes polypeptides fragments of annexin II, variants thereof, compositions that includes such fragments and/or variants, and methods of using such frag and/or variants.

19 Claims, 10 Drawing Sheets

Specification includes a Sequence Listing.

* A2OVA = same concentration as A2m
** A2OVA = same molecular ratio as A2m

* A2OVA = same moleclar ratio as OVA

Experimental Groups    n=4/treatment group

1. Saline only
2. A2OVA                   50ug/mouse
3. A2 (Scrambled)-OVA      50ug/mouse
4. A2OVA-p11 binding site  50ug/mouse Bleed all mice for:
- Dextramer
- CD8

Vaccination
Mice were vaccinated: n=4
- Saline
- A2OVA
- A2OVA-S100
- A2OVA Scrambled 2.0 mg/treatment group will be administered ip

ANNEXIN II VARIANT COMPOSITIONS AND METHODS

CROSS-REFERENCE TO RELATED APPLICATION

This application is the § 371 U.S. National Stage of International Application No. PCT/US2014/065390, filed 13 Nov. 2014, which claims priority to U.S. Provisional Patent Application Ser. No. 61/903,628, filed Nov. 13, 2013, each of which is incorporated herein by reference.

SEQUENCE LISTING

This application contains a Sequence Listing electronically submitted via EFS-Web to the United States Patent and Trademark Office as an ASCII text file entitled "110-03680201_SequenceListing_ST25.txt" having a size of 13 kilobytes. The information contained in the Sequence Listing is incorporated by reference herein.

GOVERNMENT FUNDING

This invention was made with government support under CA154345 awarded by National Institutes of Health. The government has certain rights in the invention.

BACKGROUND

An estimated 200,000 new brain tumors are diagnosed per year in North America. Of these, more than 50,000 cases are primary tumors. Primary brain cancers affect approximately 14 in 100,000 people and are responsible for more than 13,000 deaths annually. Metastatic brain tumors are more common than primary brain tumors, accounting for approximately 150,000 newly diagnosed cases per year. Lung and breast are common primary tumor sites that can metastasize to the brain.

Treatment options for certain brain tumors may be limited. For example, high-grade gliomas may be treated in some cases by surgical debulking, but surgery is not always possible. Radiation can be another option, either with or without adjuvant chemotherapy. In some cases, the preferred treatment may not provide significant long-term survival. For example, patients receiving radiotherapy for glioblastoma, even with adjuvant temozolomide chemotherapy, may face a three-year survival rate of not much more than 25%.

Another therapeutic option involves vaccines including, for example, tumor cell lysate vaccines. Such vaccines involve separately culturing monocytes obtained from a patient and tumor cells obtained from the patient, lysing the cultured tumor cells and collecting one or more antigens expressed by the culture tumor cells. The collected antigens are used to pulse dendritic cells (DCs) derived from the monocytes culture. The pulsed DCs are administered back to the patient, providing the patient with a population of DCs primed and activated by exposure to the tumor antigens, which can further prime the patient's own immune system against the tumor.

Methods that recruit a patient's immune system to help resolve tumors can benefit from advances in adjuvants that can increase the efficacy of such treatments. The 36 kDa annexin II monomer has been identified as having immunostimulatory properties.

SUMMARY OF THE INVENTION

This disclosure describes polypeptides fragments of annexin II, variants thereof, compositions that includes such fragments and/or variants, and methods of using such fragments and/or variants.

In one aspect, this disclosure describes an annexin II variant.

In another aspect, this disclosure describes compositions that include an annexin II variant. In some embodiments, such a composition can further include at least one antigen and/or a second adjuvant. In some of these embodiments, the antigen and/or second adjuvant may be coupled to the annexin II variant.

In another aspect, this disclosure describes a method that generally includes administering to a subject in need of such treatment an effective amount of composition that includes an annexin II variant.

In another aspect, this disclosure describes a method that generally includes contacting dendritic cells with a composition that includes an annexin II variant and an antigen. In some embodiments, the method can further include subsequently administering the dendritic cells to a subject.

DETAILED DESCRIPTION OF ILLUSTRATIVE EMBODIMENTS

Figure 1:
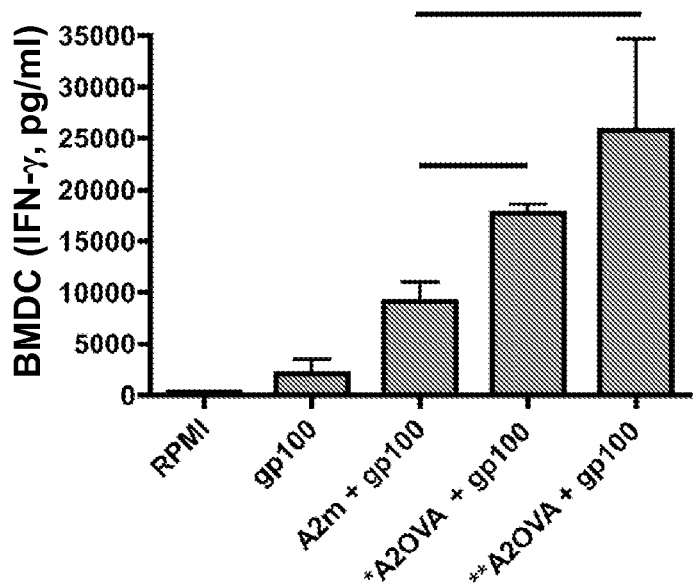
FIG. 1. Data showing adjuvant activity of annexin II N-terminus.

This disclosure describes polypeptide fragments of annexin II and variants thereof. The fragments and/or variants can exhibit annexin II activity, including therapeutic activity. Because the fragments and/or variants are smaller than the full length annexin II protein, they may be more easily used in pharmaceutical compositions.

Throughout the description that follows, the following terms shall have the indicated meanings.

"Antigen" and variations thereof refer to any material capable of inducing an immune response in a subject challenged with the material. In various embodiments, an antigen may induce a cell-mediated immune response, a humoral immune response, or both. Suitable antigens may be synthetic or occur naturally and, when they occur naturally, may be endogenous (e.g., a self-antigen) or exogenous. Suitable antigenic materials include but are not limited to peptides or polypeptides (including a nucleic acid, at least a portion of which encodes the peptide or polypeptide); lipids; glycolipids; polysaccharides; carbohydrates; polynucleotides; prions; live or inactivated bacteria, viruses, fungi, or parasites; and bacterial, viral, fungal, protozoal, tumor-derived, or organism-derived immunogens, toxins or toxoids.

"Moiety" and variations thereof refer to a portion of a chemical compound that exhibits a particular character such as, for example, a particular biological or chemical function (e.g., immunomodulation and/or target specificity).

"Prophylactic" and variations thereof refer to a treatment that limits, to any extent, the development and/or appearance of a symptom or clinical sign of a condition (e.g., a neoplastic condition or an infectious condition), including preventing or limiting initial development and/or appearance of the condition, preventing or limiting the spread of an existing subclinical condition, or both. "Subclinical" refers to the state of a condition prior to manifestation of a symptom or sign of the condition.

"Sign" or "clinical sign" refers to an objective physical finding relating to a particular condition capable of being found by one other than the patient.

"Stabilizing moiety" refers to that portion of a composition that possesses functional activity that increases the stability of the composition in the body compared to a corresponding composition without the stabilizing moiety.

"Symptom" refers to any subjective evidence of disease or of a patient's condition.

"Targeting moiety" refers to that portion of a composition that possesses target-specific affinity. The targeting moiety may be, or be derived from, an antibody, but may, alternatively, be or be derived from a non-antibody protein or peptide, or non-protein material including, for example, a small molecule.

"Therapeutic" and variations thereof refer to a treatment that ameliorates one or more existing symptoms or clinical signs associated with a condition.

"Treat" or variations thereof refer to reducing, limiting progression, ameliorating, or resolving, to any extent, the symptoms or signs related to a condition. "Ameliorate" refers to any reduction in the extent, severity, frequency, and/or likelihood of a symptom or clinical sign characteristic of a particular condition.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

The annexin protein family includes at least ten genes in mammals. Annexins generally bind calcium and phospholipids in the presence of calcium Annexin II (also sometimes referred to "annexin A2" or "AII") is an abundant annexin that is known to exist as a monomer (AIIm, 36 kDa), a heterodimer (AIId) or a heterotetramer (AIIt). The heterodimer includes one AIIm subunit and one subunit of 3-phosphoglycerate kinase. The heterotetramer includes two AIIm subunits and two 11 kDa subunits.

The 36 kDa annexin II monomer possesses immune response modifier activity (International Patent Application No. PCT/US2011/055211; U.S. Patent Application Publication No. 2013/0331546 A1). This disclosure reports identification of a fragment of the annexin II 36 kDa monomer that possesses annexin II activity and variants of the fragment. For brevity in the description that follows, unless otherwise specified, reference to annexin II refers to the 36 kDa monomer as opposed to the heterodimer or heterotetramer. Reference to an "annexin II variant" refers to a fragment of the 36 kDa monomer or a modified form of such a fragment. A modified form of a fragment of the 36 kDa annexin II monomer can be any polypeptide possessing a measurable level of annexin II activity and structural similarity to a corresponding reference amino acid sequence of a corresponding portion of the wild type 36 kDa annexin II monomer. Also, because an annexin II variant refers to a fragment of the 36 kDa monomer, an annexin II variant necessary includes less than the full length annexin II amino acid sequence. Accordingly, discussion of embodiments of annexin II variants that can include additional amino acid residues necessarily, by definition, excludes the full length wild type annexin II polypeptide.

As used herein, a polypeptide is "structurally similar" to a reference wild type annexin II fragment amino acid sequence if the amino acid sequence of the polypeptide possesses a specified amount of identity compared to the reference amino acid sequence. Structural similarity of two polypeptides can be determined by aligning the residues of the two polypeptides (for example, a candidate polypeptide and the polypeptide of, for example, any one of SEQ ID NO:1-6) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide (e.g., any one of SEQ ID NO:1-6). A candidate polypeptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide of the invention may be selected from other members of the class to which the amino acid belongs. For example, it is well-known in the art of protein biochemistry that an amino acid belonging to a grouping of amino acids having a particular size or characteristic (such as charge, hydrophobicity or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a polypeptide containing deletions or additions of one or more contiguous or noncontiguous amino acids that do not eliminate a functional activity of the polypeptide are also contemplated.

An annexin II variant can therefore include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to an appropriate wild type annexin II fragment reference amino acid sequence.

In certain embodiments, an annexin II variant can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an appropriate wild type annexin II fragment reference amino acid sequence.

An annexin II variant also can be designed to provide additional sequences, such as, for example, additional C-terminal or N-terminal amino acids that can, for example, facilitate purification by trapping on columns or use of antibodies. Such tags include, for example, histidine-rich tags that allow purification of polypeptides on nickel columns.

In some embodiments, an annexin II variant can include an amino acid sequence that incorporates one or more amino acid substitution regardless of whether each amino acid substitution is naturally occurring or engineered (e.g., using recombinant or other laboratory techniques). In some embodiments, an annexin II variant can include a combination of amino acid substitutions and each one, independently of every other substitution, may be naturally occurring or engineered. Exemplary annexin II variants are reflected in the amino acid sequences of SEQ IS NO:12-26. One such embodiment, having an alanine for isoleucine substitution at position six (I6A, A-6, Table 1, below) of a 15 amino acid annexin II fragment, possesses an increase in annexin II activity (FIGS. 7, 9, 11, and 12).

The 36 kDa annexin II monomer possesses immune response modifier activity (International Patent Application No. PCT/US2011/055211; U.S. Patent Application Publication No. 2013/0331546 A1) Annexin II can increase the efficacy of vaccines that rely on CD8+ T cell responses to mediate a therapuetic or prophylactic effect. Accordingly, compositions that include annexin II may be useful as adjuvants in immunotherapies such as, for example, cancer vaccines and vaccines directed against infectious agents (e.g., viruses, bacteria, parasites).

Thus, as used herein, "annexin II activity" includes modulating an immune response. For example, "annexin II activity" can include re-routing endocytosed antigen to the MHC I molecule without appreciably changing co-stimulatory molecule expression, possessing Toll-like receptor 2 (TLR2) agonist activity, possessing Toll-like receptor 4 (TLR4) agonist activity, selectively increasing antigen presentation on MHC I, downregulating "type II" cytokine production (eg, IL-10, IL-4), inducing type I cytokine secretion (eg, IL-12, TNF-α, IL-1β), enhancing dendritic cell maturation, enhancing B cell maturation, and/or stimuating production of antibodies or T cells.

Annexin II N-Terminal Fragment as an Adjuvant

Figure 2:
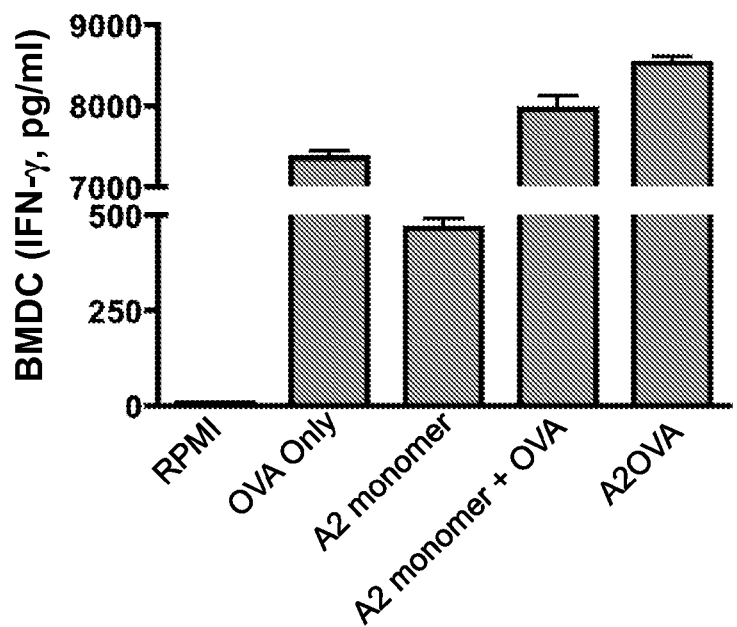
FIG. 2. Data demonstrating enhancement of IFN-γ response to OVA model antigen using, as an adjuvant, an annexin II N-terminus peptide.
Figure 3:
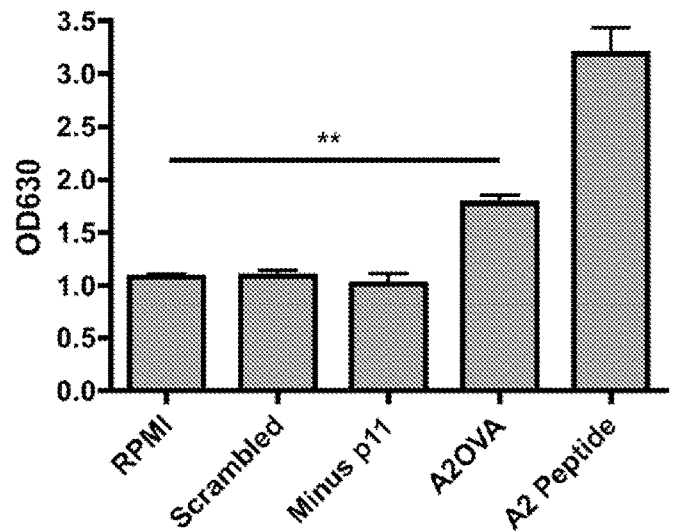
FIG. 3. Data showing that activity of annexin II-OVA fusion protein is TLR2-mediated.

To test if the 35 amino acid N-terminus of annexin II, which distinguishes annexin II from other annexins, contains adjuvant activity, we pulsed bone marrow-derived dendritic cells (BMDC) with gp100+/−A2OVA, fusion peptide containing this 35 amino acid fragment. A2OVA exerted adjuvant activity in both equal concentrations and molecular ratio compared to full-length annexin II protein in a measure of the gp100-specific CD8 T cell response (FIG. 1). We then tested whether this fusion peptide enhanced adjuvant activity over that of addition of OVA and full length annexin II protein. BMDC were pulsed with A2OVA and we measured the OVA-specific OT-1 CD8 T cell response. A2OVA fusion peptide induced an IFNγ response superior to that of A2 monomer (A2m)+OVA added as separate agents (FIG. 2). To further investigate the ability to derive a novel single antigen fusion peptide, we constructed OVA fusion peptides in which an OVA peptide (SEQ ID NO:9) was fused to either an annexin II N-terminal fragment or a scrambled 35 amino acid peptide to produce SEQ ID NO:30 and SEQ ID NO:29, respectively. Peptides were pulsed on TLR2 transfected cells and alkaline phosphatase activity was used to determine NF-κB activity (FIG. 3). A2OVA fusion protein stimulated NF-κB through TLR2. However, to our surprise, the fusion protein (SEQ ID NO:30) lacking the most terminal annexin II amino acids did not elicit a response.

Annexin II-OVA Fusion Peptide Stimulates an Antigen Specific T Cell Response In Vivo Next, we investigated the use of the A2OVA in vivo. A2OVA peptide (SEQ ID NO:32) was given to non-tumor bearing mice as described in FIG. 4A to see if they would elicit an OVA specific T cell response. A2OVA fusion peptide stimulated an antigen specific $CD8^+$ T cell response in vivo (FIG. 4B). To determine if the 35 amino acid annexin II fragment can extend survival in tumor bearing animals in an antigen non-specific manner, we used breast tumor bearing BALB/c mice, which lack the MHC haplotype to present SIINFEKL. Mice were treated with A2OVA peptide as summarized in FIG. 5A and followed for survival. Mice injected with A2OVA peptide demonstrated enhanced survival compared to saline or scrambled control. Once again, the first 15 N-terminal amino acids were required, as the A2OVA-S100 (otherwise referred to herein as A2OVA-pp11, SEQ ID NO:30) conferred no survival benefit (FIG. 5B).

Figure 6:
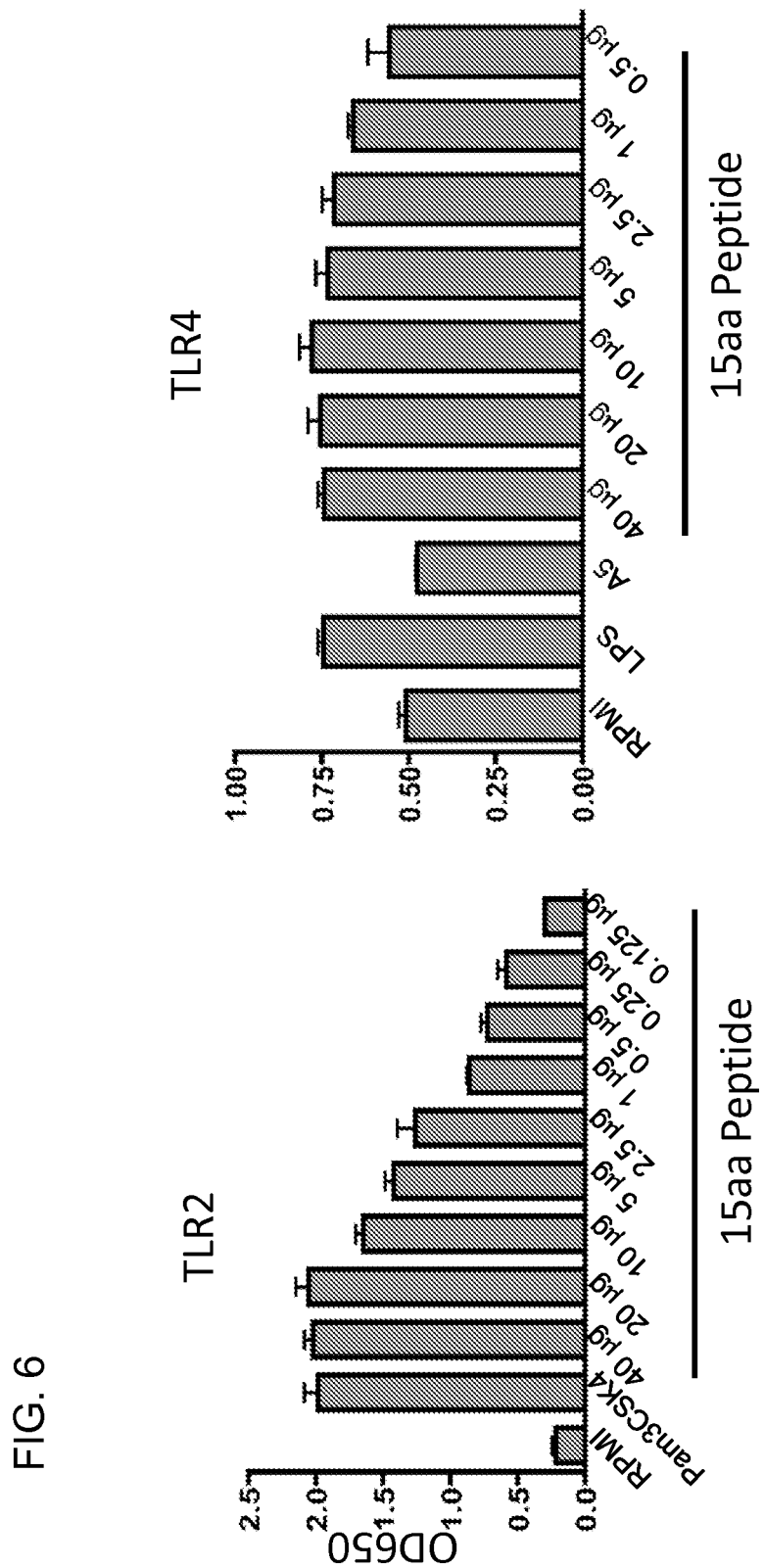
FIG. 6. Data demonstrating annexin II activity of the 15 N-terminal amino acid peptide.

The N-Terminal 15 Amino Acids of Annexin II have TLR2 Agonist Activity and TLR4 Agonist Activity To better characterize the 35 amino acid N-terminus as an adjuvant, we serially removed five amino acids from the C-terminus end of the N-terminal fragment to produce annexin II variants SEQ ID NO:2, SEQ ID NO:3, SEQ ID NO:4, SEQ ID NO:5, and SEQ ID NO:6. We tested the resulting peptides for NF-κB activity. The annexin II fragment consisting of the most N-terminal 15 amino acids (SEQ ID NO:5) activated TLR2 and, to a lesser extent, TLR4 (FIG. 6). To test the ability of the 15 amino acid annexin II fragment (SEQ ID NO:5) to stimulate an immune response, and to determine whether its ability to do so is mediated through TLR2, wild-type and TLR-2 knockout mice were given OVA±annexin II or OVA±the 15 amino acid N-terminal annexin II fragment (SEQ ID NO:5).

A 15 Amino Acid Annexin II N-Terminal Fragment Induces Cytokine Secretion from Bone Marrow Derived Dendritic Cells (BDMCs)

Figure 7:
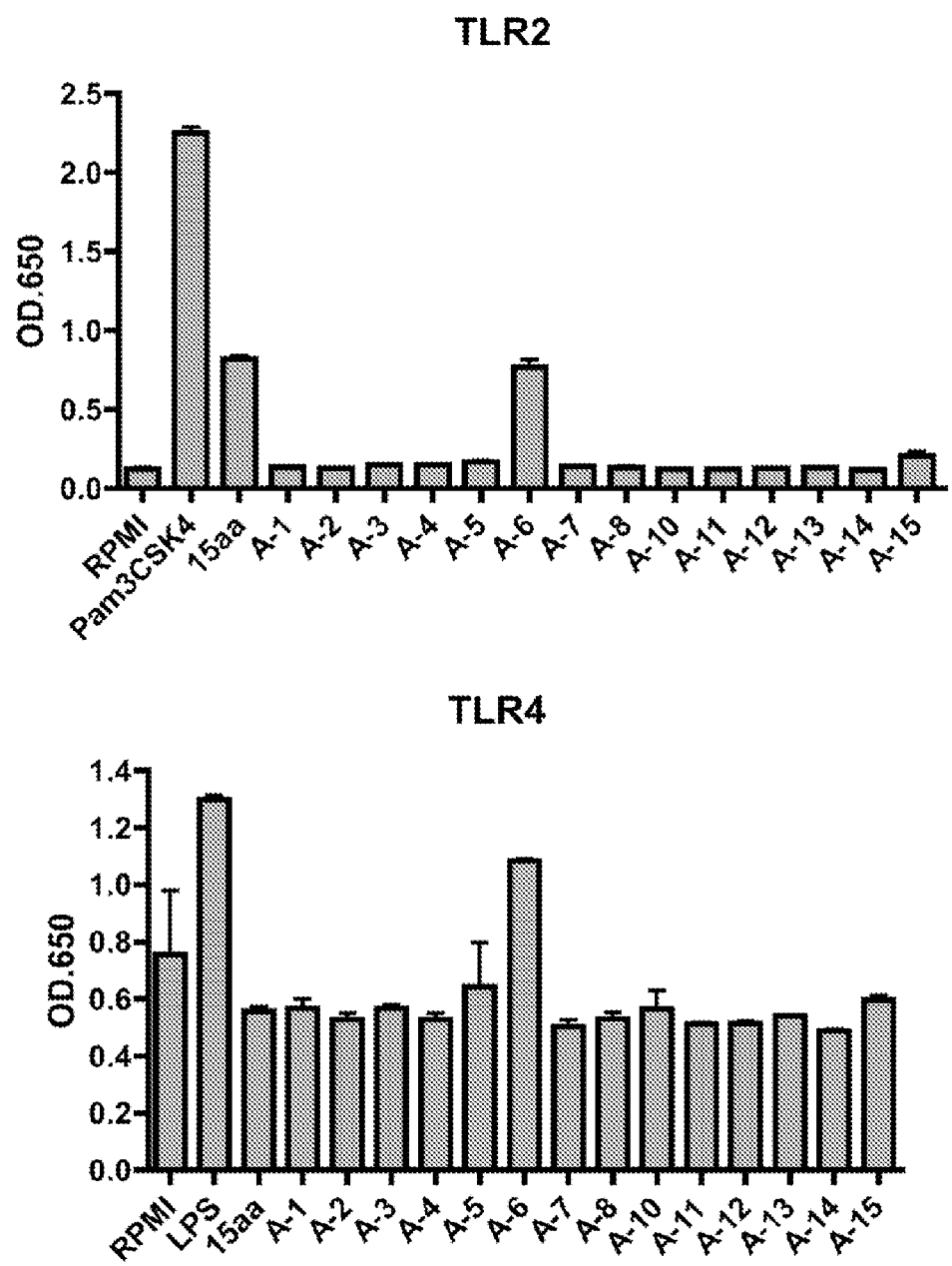
FIG. 7. Data demonstrating annexin II activity of annexin II variants.
Figure 9:
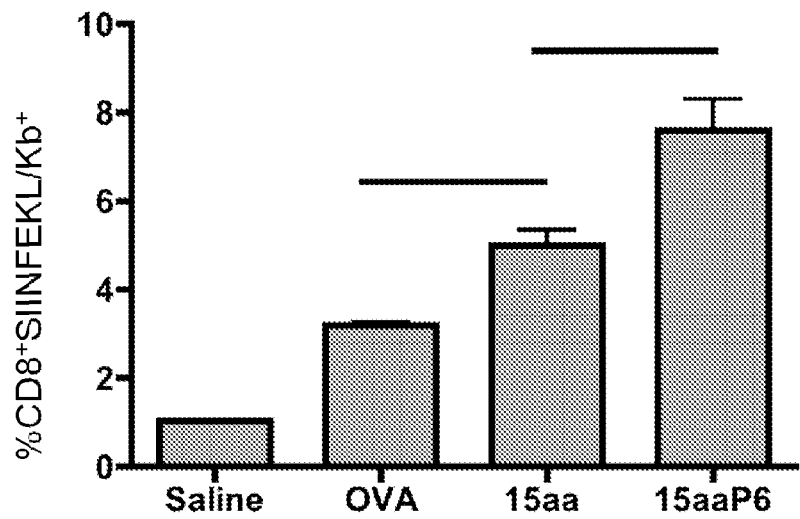
FIG. 9. Data comparing in vivo annexin II activity of the 15 amino acid N-terminal annexin II fragment and an annexin II variant.
Figure 10:
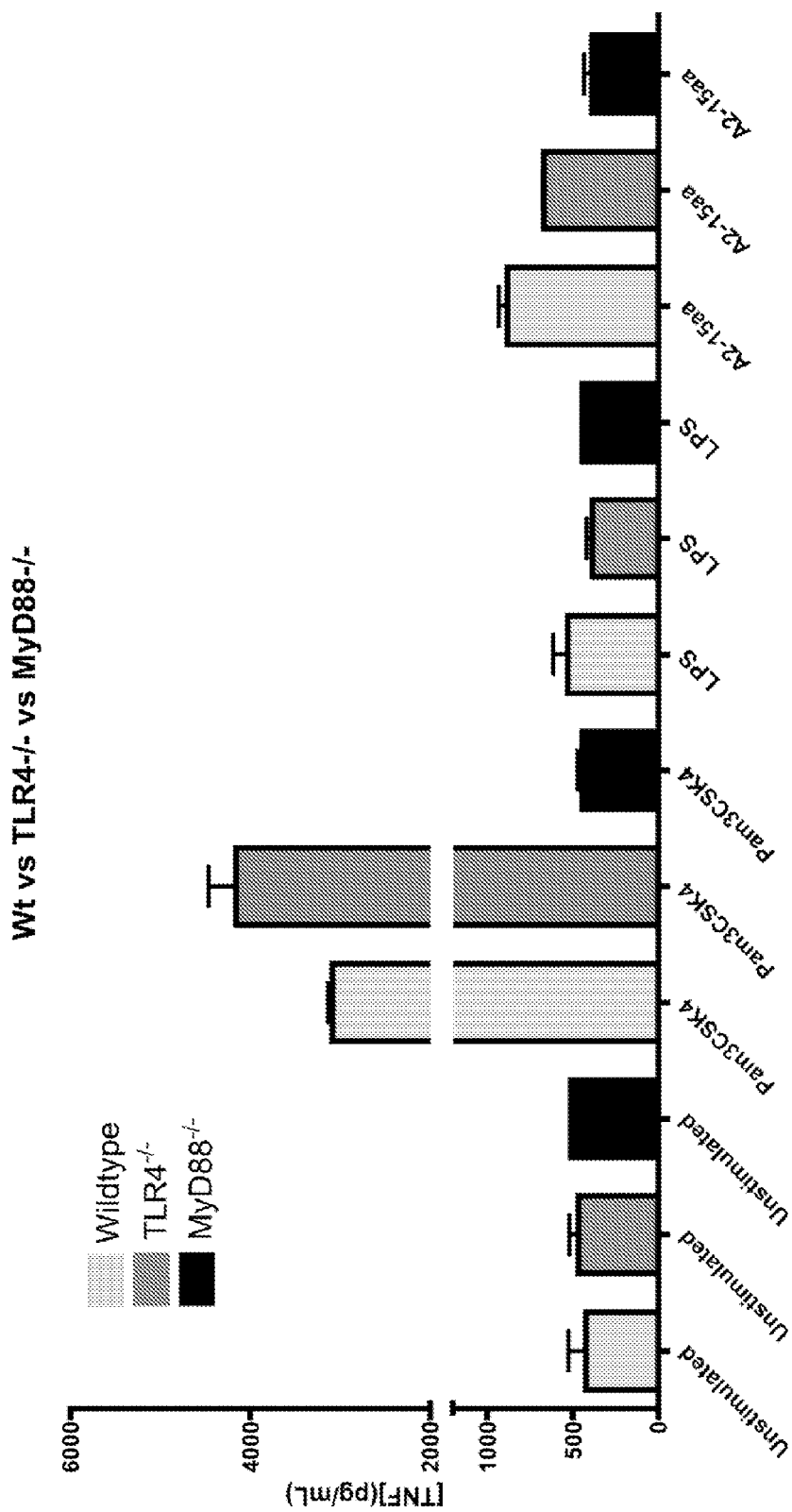
FIG. 10. Data comparing in vitro annexin II activity of full length annexin II and the 15 amino acid N-terminal annexin II fragment.

To determine the 15 amino acid N-terminal annexin II fragment's activity on dendritic cells, BMDCs were derived for wild-type, TLR4 knockout, and MyD88 knockout mice. The various BMDCs and pulsed with the 15 amino acid N-terminal annexin II fragment (SEQ ID NO:5). This demonstrated that the 15 amino acid N-terminal annexin II fragment (SEQ ID NO:5) mediated induction of TNF secretion and that the activity is MyD88-dependent (FIG. 10). Substituting Isoleucine with Alanine at the 6th N-Terminal Amino Acid Enhances TLR2 and TLR4 Signaling To further characterize the 15 amino acid N-terminal annexin II fragment, we constructed variants of the fragment in which each fragment harbored a single amino acid substitution of an alanine for a different amino acid. The variants are listed in Table 1. The variant harboring an isoleucine to alanine substitution (A-6, SEQ ID NO:17) exhibited enhanced TLR2 and TLR4 signaling (FIG. 7). In addition, the A-6 variant (SEQ ID NO:17) can induce enhanced OVA specific T cell priming in vivo (FIG. 9, 15aaP6).

Figure 11:
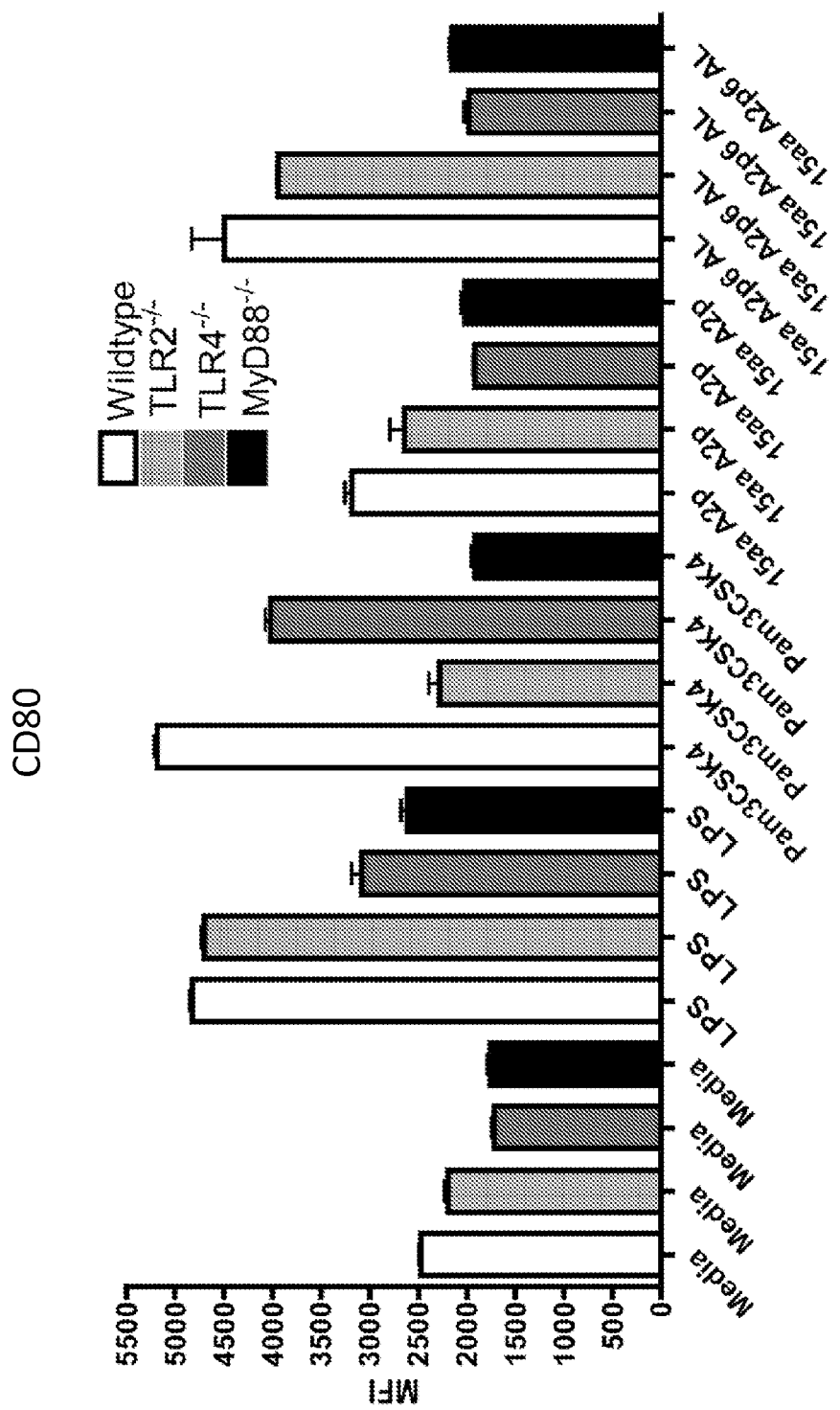
FIG. 11. Data comparing in vitro annexin II activity of the 15 amino acid N-terminal annexin II fragment and an annexin II variant.
Figure 12:
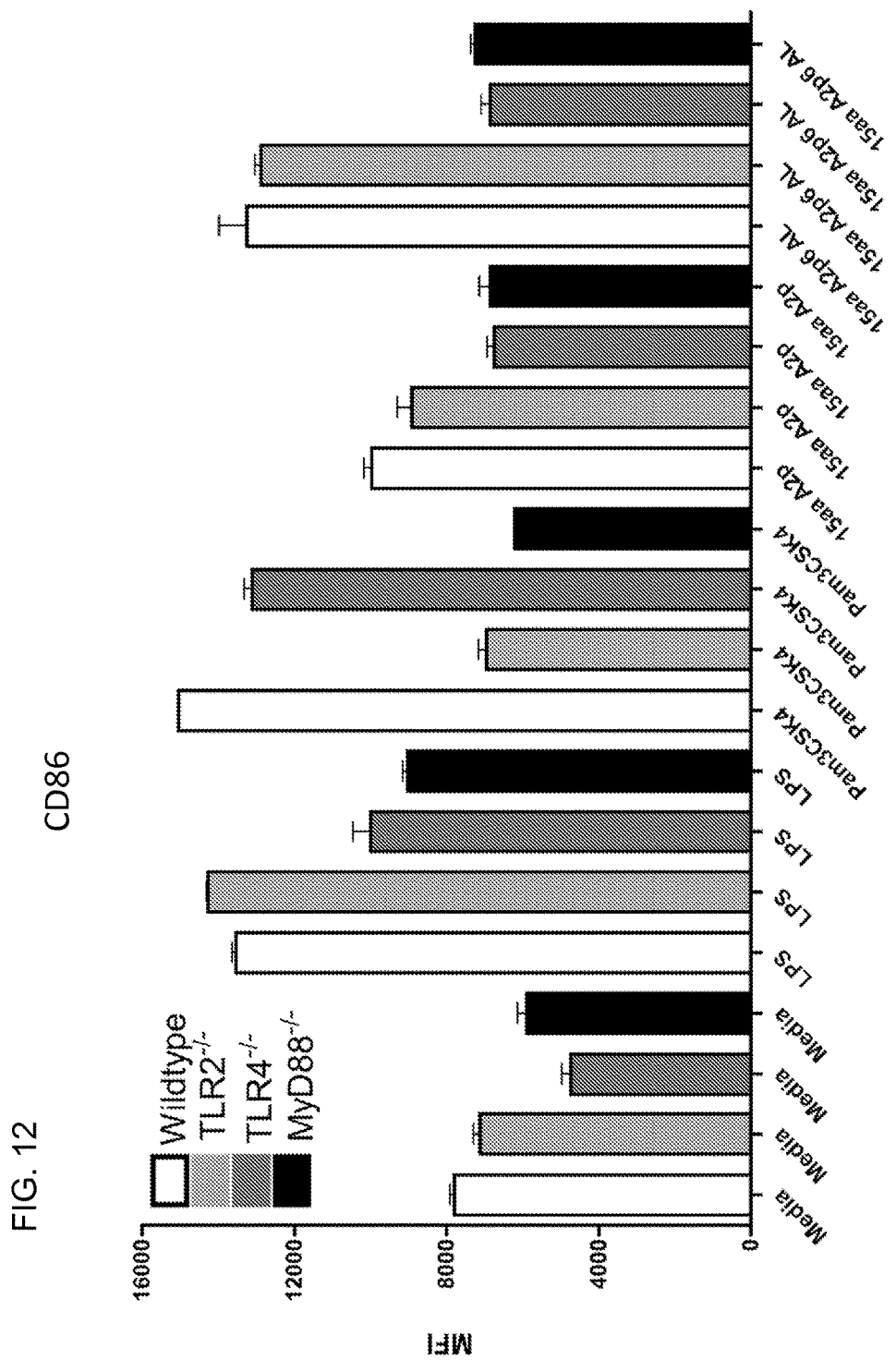
FIG. 12. Data comparing in vitro annexin II activity of the 15 amino acid N-terminal annexin II fragment and an annexin II variant.

To further characterize the activity of the A-6 variant (SEQ ID NO:17), BMDCs from wild-type, TLR2 knockout, TLR4 knockout, and MyD88 knockout mice were pulsed with the peptide and analyzed for co-stimulatory molecules CD80 (FIG. 11) and CD86 (FIG. 12). Both the 15 amino acid N-terminal fragment (SEQ ID NO:5) and the A-6 variant (SEQ ID NO:17) increased CD80 and CD86 co-stimulatory molecule expression in a TLR4- and MyD88-dependent manner.

Accordingly, in one aspect, this disclosure describes a composition that includes an annexin II variant such as, for example, an immunomodulatory fragment of annexin II. One can determine whether an annexin II variant possesses immunomodulatory activity by any suitable method including, for example, any method described herein. However, other standard assays of immunomodulatory activity are well within the skill of a person of ordinary skill in the art.

In some embodiments, an annexin II variant can include a N-terminal portion of annexin II such as, for example, any one of the amino acid sequences reflected in SEQ ID NO:1-6. In some of these embodiments, the annexin II variant can include a 15 amino acid fragment of annexin II (e.g., SEQ ID NO:5) or a modified form thereof (e.g., any one of SEQ ID NO:12-26). In one particular embodiment (SEQ ID NO:17), the annexin II variant can include an alanine for isoleucine amino acid substitution at position six (I6A, A-6 in Table 1) of the 15 amino acid fragment shown in SEQ ID NO:5.

A composition can include multiple annexin II variants. Thus, in some embodiments, a composition can include a fusion polypeptide that includes a plurality of annexin II variants.

In some cases, a composition can further include one or more antigens against which an immune response is desired. While described herein in the context of an exemplary embodiment in which the antigen is the model antigen ovalbumin, the compositions and methods described herein can involve using any antigen of interest. Thus, the antigen may be, for example, a tumor antigen or an antigen expressed by an infectious agent. In certain embodiments, the antigen may be derived from a tumor cell lysate. Exemplary tumor antigens include, for example, gp100 (a melanoma-associated antigen), IL13rα2, Epha2 (ephrin type-A receptor 2), immunogenic fragments thereof, and fusions of such antigens and/or fragments.

In some embodiments, the annexin II variant and the antigen may be provided in admixture, suspension, emulsion, etc. If provided in an emulsion, it is possible for the annexin II variant and the antigen to be provided in separate phases of the emulsion.

In other embodiments, the annexin II variant and the antigen may be coupled so that the antigen and annexin II variant, as an adjuvant, may be co-presented to cells of the immune system. The annexin II variant and antigen may be covalently coupled (e.g., crosslinking), affinity coupled (e.g., avidin-biotin), or coupled as a fusion polypeptide. The construction of such embodiments are described in Example 3.

In yet another embodiment, a polynucleotide that encodes an annexin II variant (hereinafter, an annexin II variant polynucleotide) coding sequence—e.g., a nucleotide sequence that encodes any annexin II variant (e.g., a nucleotide sequence that encodes the amino acid sequence of any one of SEQ ID NO:1-6, 12-26)—may be cloned into the genome of an attenuated virus so that the virus capsid includes at least one annexin II variant. When the virus is made, the capsid surface may be decorated with at least one annexin II variant that can enhance the anti-virus immune response. This approach also may be useful for treating certain bacterial diseases. For example, an annexin II variant polynucleotide may be cloned into an attenuated tuberculosis-causing *mycobacterium* such as, for example, *Mycobacterium tuberculosis* so that the microbe expresses the annexin II variant.

In some embodiments, an annexin II variant may be coupled to a targeting moiety. The targeting moiety of the composition may be any material that can provide targeted delivery of the composition. In many embodiments, the targeting portion may provide immunospecific targeting—i.e., may be a sufficient portion of an immunoglobulin (i.e., an antibody) to promote immunospecific binding of the composition to a target antigen. However, such embodiments may be practiced using non-immunoglobulin targeting materials as well such as, for example, certain small molecules or receptor ligands such as, for example, hormones (natural or synthetic), lipids, etc. As used herein, "specific" and variations thereof (e.g., "immunospecific," having "specificity," etc.) relate to having a differential or a non-general affinity, to any degree, for a particular target.

Thus, in some embodiments, an annexin II variant may be coupled to an anti-tumor targeting moiety such as, for example, a ligand of a tumor-specific marker, an anti-tumor antibody, or a moiety derived from an anti-tumor antibody. As used herein, an anti-tumor antibody refers to an antibody (Ab) that recognizes cells of a tumor with some degree of specificity over normal tissue cells. The coupled annexin II variant/Ab composition can exploit the tumor specificity provided by the antibody to target delivery of the coupled annexin II variant to the vicinity of tumor antigens.

Because anti-tumor antibodies, like all immunoglobulins, are proteins, modifications can be made to a particular anti-tumor antibody without rendering the modified anti-tumor antibody unsuitable for use as a targeting moiety. For example, one or more portions of the anti-tumor antibody amino acid sequence may be deleted or substituted, or additional amino acids may be added to an anti-tumor antibody, and the anti-tumor antibody can still retain sufficient immunospecific character to be suitable for practicing the invention. Therefore, in the description that follows, reference to a particular anti-tumor antibody includes modified anti-tumor antibodies that have such modifications (e.g., amino acid additions, deletions, and/or substitutions) as are possible while retaining a sufficient amount of the antibody's immunospecific character.

Thus, generally, a targeting moiety can include an antibody that targets, for example, a microbial antigen (e.g., bacterial, viral, parasitic or fungal antigens), a cancer or a tumor-associated antigen, an immune cell, and/or a self-antigen. In many embodiments, a suitable antibody is one that recognizes and binds to an antigen present on or in a cell. An antibody that binds to a particular material (i.e., Antigen) may be referred to, interchangeably, as "anti-Antigen" or an "Antigen antibody". In some instances, an antibody may be referred to by a generic name or commercial tradename.

Exemplary antibodies include, but are not limited to, rituximab, an anti-CD20 antibody (e.g., RITUXAN, Genentech, Inc., South San Francisco, Calif./Biogen Idec, Cambridge, Mass.); trastuzumab (e.g., HERCEPTIN, Genentech, Inc., South San Francisco, Calif.); samarium ($^{153}$Sm) lexidronam (samarium-153-ethylene diamine tetramethylene phosphonate, abbreviated Samarium-153 EDTMP, e.g., QUADRAMET, Lantheus Medical Imaging, Inc., North Billerica, Mass.); edrecolomab (MAb17-1A, e.g., PAN-OREX, Centocor Ortho Biotech, Inc., Horsham, Pa.); IDEC-Y2B8; BEC2 (an anti-idiotypic monoclonal antibody that mimics GD3); cetuximab (C225, and anti-EGFR monoclonal antibody, e.g., ERBITUX, ImClone LLC, New York, N.Y.)); an anti-Lym1 antibody (e.g., ONCOLYM, Alpha Therapeutic Corp., Los Angeles, Calif.); SMART M195 (e.g., ZAMYL, Protein Design Labs, Inc., Freemont, Calif.); tretinoin (e.g., ATRAGEN, Genzyme Corp., Cambridge, Mass.); an anti-CA125 antibody (e.g., OVAREX, AltaRex Medical Corp., Edmonton, AB, Canada); tositumomab (e.g., BEXXAR, GlaxoSmithKline LLC, Wilmington, Del.); LDP-03; ior t6; the FcγR1 (CD64)/HER-2/new bispecific antibody MDX-210; MDX-11; MDX-22; OV103; anti-interleukin-2 monoclonal antibody 3622W94; an anti-VEGF antibody; daclizumab (e.g., ZENAPAX, Hoffman-LaRoche AG, Basel, Switzerland); anti-TAG-72 (MDX-220); the FcγR1 (CD64)/EGFR bispecific antibody MDX-447; MELIMMUNE-1 (Biogen idec, Cambridge, Mass.); MELIMMUNE-2 (Biogen idec, Cambridge, Mass.); labetuzumab (e.g., CEA-CIDE, Immunomedics, Inc., Morris Plains, N.J.); PRETARGET, Aletheon Pharmaceuticals, Inc., Seattle, Wash.); GNI-250; matuzumab (e.g., EMD-72000, Merck Serono, Darmstadt, Germany); epratuzumab (e.g., LYMPHOCIDE, Immunomedics, Inc., Morris Plains, N.J.); gemtuzumab zogamicin (CMA-676, e.g., MYLOTARG, Pfizer Inc., New York, N.Y.); Monopharm-C; anti-Her-2/neu monoclonal antibody 4B5 (Ventana Medical Systems, Inc., Tucson, Ariz.); anti-EGFR monoclonal antibody ior egf.r3; anti-tumor associated antigen (TAA) monoclonal antibody ior c5; an anti-FLK-2 antibody; the FcγR1 (CD64)/HER-2/new bispecific antibody MDX-260; an antinuclear antibody (ANA Ab); SMART ID10Ab; SMART ABL 364 Ab; the anti-TAG72 monoclonal antibody CC49; ImmuRAIT-CEA (Immunomedics, Inc., Morris Plains, N.J.); an anti-IL-4 antibody; an anti-IL-5 antibody; an anti-IL-9 antibody; an anti-Ig antibody; an anti-IgE antibody; a serum-derived hepatitis B antibody; a recombinant hepatitis B antibody; an anti-CD40 antibody; an anti-OX40 antibody; an anti-Cytokine Receptor antibody; and the like.

Other antibodies similarly useful in the composition and/or methods described herein—and medical indications for which each may be useful—include alemtuzumab (B cell chronic lymphocytic leukemia), gemtuzumab ozogamicin (CD33+ acute myeloid leukemia), hP67.6 (CD33+ acute myeloid leukemia), infliximab (inflammatory bowel disease and rheumatoid arthritis), etanercept (rheumatoid arthritis), tositumomab, MDX-210, oregovomab, anti-EGF receptor mAb, anti-tissue factor protein (TF), edrecolomab, ibritumomab tiuxetan, anti-idiotypic mAb mimic of ganglioside GD3 epitope, anti-HLA-Dr10 mAb, anti-CD33 humanized mAb, anti-CD52 humAb, anti-CD1 mAb (ior t6), MDX-22, celogovab, anti-17-1A mAb, bevacizumab, anti-idiotypic mAb mimic of high molecular weight proteoglycan (I-Mel-1), anti-idiotypic mAb mimic of high molecular weight proteoglycan (I-Mel-2), anti-CEA Ab, hmAbH11, anti-DNA or DNA-associated proteins (histones) mAb, Gliomab-H mAb, GNI-250 mAb, anti-CD22, CMA 676), anti-idiotypic human mAb to GD2 ganglioside, for egf/r3, anti-ior c2 glycoprotein mAb, anti-FLK-2/FLT-3 mAb, anti-GD-2 bispecific mAb, antinuclear autoantibodies, anti-HLA-DR Ab, anti-CEA mAb, palivizumab, alemtuzumab, BLyS-mAb, anti-VEGF2, anti-Trail receptor; B3 mAb, mAb BR96, and Abx-Cb1 mAb.

Suitable antibodies also include the following:

Antibodies that target antigen presenting cells such as, for example, anti-Dec205, anti-MHC II, anti-CD11c.

Apoptosis antibodies such as, for example, Fas/Fas Ligand antibodies including, but not limited to, anti-human Fas/Fas Ligand antibodies, anti-murine Fas/Fas Ligand antibodies, Granzyme antibodies, Granzyme B antibodies; Bcl Antibodies including, but not limited to, anti-cytochrome C antibodies, anti-human Bcl antibodies (monoclonal), anti-human Bcl antibodies (polyclonal), anti-murine Bcl Antibodies (monoclonal), and anti-murine Bcl antibodies (polyclonal);

Miscellaneous apoptosis antibodies such as, for example, anti-TRADD, anti-TRAIL, and anti-DR3 antibodies;

Miscellaneous apoptosis-related antibodies such as, for example, Bim antibodies including, but not limited to, anti-human, murine bim antibodies (polyclonal), anti-human, murine bim antibodies (monoclonal);

Caspase antibodies such as, for example, anti-human caspase antibodies (monoclonal), and anti-murine caspase antibodies;

Anti-CD antibodies such as, for example, anti-CD25, anti-CD29, anti-CD29, anti-CD41a, anti-CD42b, anti-CD42b, anti-CD42b, anti-CD43, anti-CD46, anti-CD61, anti-CD61, anti-CD62/P-slctn, anti-CD62/P-slctn, and anti-CD154;

Human chemokine antibodies such as, for example, human CNTF antibodies, human eotaxin antibodies, human epithelial neutrophil activating peptide-78 (ENA-78) antibodies, human exodus antibodies, human GRO antibodies, human HCC-1 antibodies, human 1-309 antibodies, human IP-10 antibodies, human I-TAC antibodies, human LIF antibodies, human liver-expressed chemokine (LEC) antibodies, human lymphotaxin antibodies, human MCP antibodies, human MIP antibodies, human monokine induced by IFN-γ (MIG/CXCL9) antibodies, human NAP-2 antibodies, human NP-1 antibodies, human platelet factor-4 antibodies, human RANTES antibodies, human SDF antibodies, and human TECK antibodies;

Murine chemokine antibodies such as, for example, human B-cell attracting murine chemokine antibodies, chemokine-1 antibodies, murine eotaxin antibodies, murine exodus antibodies, murine GCP-2 antibodies, murine KC antibodies, murine MCP antibodies, murine MIP antibodies, and murine RANTES antibodies;

Rat Chemokine Antibodies such as, for example, rat CNTF antibodies, rat GRO antibodies, rat MCP antibodies, rat MIP antibodies, and rat RANTES antibodies;

Cytokine/cytokine receptor antibodies such as, for example, human biotinylated cytokine/cytokine receptor antibodies, human interferon (IFN) antibodies, human interleukin (IL) antibodies, human leptin antibodies, human oncostatin antibodies, human tumor necrosis factor (TNF) antibodies, human TNF receptor family antibodies, murine biotinylated cytokine/cytokine receptor antibodies, murine IFN antibodies, murine IL antibodies, murine TNF antibodies, murine TNF receptor antibodies, rat biotinylated cytokine/cytokine receptor antibodies, rat IFN antibodies, rat IL antibodies, and rat TNF antibodies;

Extracellular matrix antibodies such as, for example, collagen/procollagen antibodies, laminin antibodies, human collagen antibodies, human laminin antibodies, human procollagen antibodies, vitronectin/vitronectin receptor antibodies, human vitronectin antibodies, human vitronectin receptor antibodies, fibronectin/fibronectin receptor antibodies, human fibronectin antibodies, and human fibronectin receptor antibodies;

Growth factor antibodies such as, for example, human growth factor antibodies, murine growth factor antibodies, and porcine growth factor antibodies;

Miscellaneous antibodies such as, for example, baculovirus antibodies, cadherin antibodies, complement antibodies, C1q antibodies, VonWillebrand factor antibodies, Cre Antibodies, HIV Antibodies, influenza antibodies, human leptin antibodies, murine leptin antibodies, murine CTLA-4 antibodies, P450 antibodies, and RNA polymerase antibodies; and Neurobiological antibodies such as, for example, amyloid antibodies, GFAP antibodies, human NGF antibodies, human NT-3 antibodies, and human NT-4 antibodies.

Additional antibodies suitable for use in the invention include, for example, antibodies listed in references such as the MSRS Catalog of Primary Antibodies and Linscott's Directory.

In some embodiments, the targeting moiety may include, instead of a full antibody, an antibody fragment. An antibody fragment can be obtained by digesting (with, for instance, pepsin or papain) a whole antibody by any conventional method to produce, for example, a 5S fragment denoted F(ab')2, a 3.5S Fab' monovalent fragment, a monovalent Fab' fragment, and/or an Fc fragment. Alternatively, an antibody fragment can be prepared by routine known methods including expression in a heterologous host cell (e.g., $E.$ $coli$) of a polynucleotide encoding the fragment.

Small molecule target moieties can include, for example, ligands of markers expressed by target cells. In some cases, the targeting moiety can include a ligand of TLR2 (Toll-like receptor 2). Exemplary TLR2 ligands include, for example, polyICLC, resiquimod, imiquimod, CpG ODN, flagellin, PAMCys3K, MALP2, and lipopolysaccharide (LPS).

Additional exemplary targeting moieties include moieties that can target cells or tissues such as, for example, cells of the immune system or endothelial tissues.

In some alternative embodiments, an annexin II variant may be coupled to a dendritic cell targeting moiety. The targeting moiety may be an antibody (e.g., an anti-DC antibody) or a non-antibody ligand that recognizes a DC-specific marker.

Suitable DC-specific markers may include, for example, a co-stimulatory marker such as, for example, any member of the TNFR Superfamily (e.g., CD40), CD70, CD80, CD86, B7-CD, B7.1, B7.2, etc. Other DC-specific markers include certain sugar receptors such as, for example, the mannose receptor. Thus is some embodiments, an annexin II variant may be coupled with a sugar such as, for example, mannose, to target delivery of the annexin II variant to, for example, antigen-presenting dendritic cells.

An immunomodulatory composition that includes a targeting moiety that recognizes a co-stimulatory marker may be used to deliver two DC-activating stimuli (i.e., annexin II variant and co-stimulation) in a single chemical entity.

As used herein, an anti-DC antibody refers to an antibody that recognizes a dendritic cell antigen. A suitable dendritic cell targeting moiety may bind to any antigen that is differentially expressed, either qualitatively or quantitatively, by dendritic cells. Suitable dendritic cell targeting moieties may bind to such antigens as, for example, DEC205, BDCA-1, BDCA-2, BDCA-3, BDCA-4, DC-SIGN, L-SIGN, HLR-DR, CD11c, CD13, CD14, CD21, CD33, CD35, CD123, C-type lectins, integrins (e.g., $\alpha 4$, $\alpha 6$, $\alpha 1\beta 1$), and/or any one of the Toll-like receptors (TLRs), etc.

Regardless of whether the targeting moiety recognized a DC-specific marker or antigen, coupling an annexin II variant to the targeting moiety can limit systemic availability of the annexin II variant, even when administered via a systemic delivery route. Moreover, the annexin II variant may be concentrated in the vicinity of dendritic cells, thereby maturing and activating dendritic cells more effectively. Dendritic cells activated at the site of a tumor—or even inside a tumor mass—may be able to utilize a tumor antigen present on the surface of the tumor cells to initiate an immune response against the tumor. This method could provide a generalized anti-tumor therapy without the need for tumor-specific antibodies.

In other alternative embodiments, an annexin II variant may be coupled to an anti-macrophage targeting moiety. Macrophages are often localized in the vicinity of tumor cells. Thus, again, systemic availability of the annexin II variant can be limited and the annexin II variant may be concentrated in the vicinity of the target cells (i.e., macrophages), thereby activating macrophages more efficiently. Activated macrophages are known to possess anti-tumor activity. Thus, this method could provide a generalized tumor therapy without the need for tumor-specific antibodies.

In other alternative embodiments, an annexin II variant may be coupled to a target-specific moiety that recognizes a surface antigen on a cell type that can directly kill tumor cells such as, for example, $CD8^+$ cytotoxic T cells, NK cells, or NKT cells. Once again, even if the immunomodulatory composition is administered systemically, the annexin II variant may be concentrated in the vicinity of the tumor-killing cells, thereby (a) activating tumor-killing cells more effectively, and/or (b) limiting the systemic availability of the annexin II variant. Tumor-killing cells activated at the site of a tumor—or even inside a tumor mass—may be able to utilize a tumor antigen present on the surface of the tumor cells to initiate an immune response against the tumor. This method could provide a generalized tumor therapy without the need for tumor-specific antibodies.

In other alternative embodiments, an annexin II variant may be coupled to a targeting moiety that recognizes, for example, an endothelial target. Significant differences exist in the endothelium environments of tumor masses compared to normal capillary beds. Differences exist, for example, in the identity and extent to which certain endothelial surface proteins, adhesion molecules (e.g., integrins), extracellular matrix proteins, growth factor receptors, etc. are expressed. These differences can be exploited to target delivery of an annexin II variant to tumor-related endothelium. Some reagents that specifically target such differences have been demonstrated to be useful as anti-angiogenic therapies. Coupling such an anti-angiogenic agent—as a targeting moiety—to an annexin II variant can combine two effective anti-tumor therapies: immunotherapy and anti-angiogenesis therapy.

Suitable anti-angiogenesis reagents include, for example, anti-CD105 antibodies (CD105 is overexpressed in tumor endothelium), anti-ED-B antibodies (ED-B is a fibronectin isoform found in tumor masses), peptides recognized by endothelial integrins associated with tumors, and growth factors whose receptors are upregulated on tumor endothelium (e.g., vascular endothelial growth factor).

The use of anti-angiogenic reagents in this way may offer a combination of anti-angiogenesis and immunotherapy. Additionally, targeted delivery of an annexin II variant to the tumor endothelium, as opposed to the tumor itself, may provide more effective long-term treatment since, generally, the endothelium is a less mutagenic tissue than a tumor mass. Therefore, therapy directed toward the endothelium may be far less likely to cause drug resistance. Also, a therapy directed toward the endothelium may be effective against virtually any vascularized tumor (e.g., breast cancer, prostate cancer, lung cancer) without the need for tumor-specific reagents.

In some embodiments, an annexin II variant may be coupled to a stabilizing moiety. The stabilizing moiety may be, or be derived from, any suitable material so that the stabilizing moiety increases the stability of the composition in the body compared to a corresponding composition without the stabilizing moiety. Thus, the stabilizing moiety can increase the half-life of the composition. As used herein, "half-life" may refer to biological half-life—i.e., the time it takes for the composition to lose half of its biological activity—or may refer to plasma half-life i.e., the time is takes for the plasma concentration of the composition to decrease by half. The relationship between the biological half-life and the plasma half-life of a substance may not necessarily correlate with one another due to, for example, accumulation of the substance in tissues, the presence of active metabolites, and substance-receptor interactions. Those of ordinary skill in the art understand, for each given set of circumstances, whether biological half-life or plasma half-life is more relevant to the given set of circumstances. In some cases, the stabilizing moiety may decrease the clearance rate—i.e., the rate at which the composition is removed from the circulation by the kidneys. In other cases, the stabilizing moiety may decrease the rate at which the composition is degraded. Exemplary stabilizing moieties include, for example polyethylene glycol (PEG) and/or Fc (fragment crystallizable) region of an antibody.

The composition can further include one or more additional adjuvants. Suitable additional adjuvants include, for example, CpG nucleotides, imidazoquinoline amines, or immunomodulatory polypeptides such as, for example, various heat shock proteins. As with the annexin II variant/antigen combinations, an annexin II variant/adjuvant combination may be in admixture with one another, in co-suspension, or provided in an emulsion. When provided in an emulsion, the annexin II variant and second adjuvant may be provided in the same or in separate phases of the emulsion.

When the second adjuvant includes an immunomodulatory polypeptide, the annexin II variant and adjuvant combination may be coupled to one another so that the annexin II variant and second adjuvant can work as co-adjuvants. The annexin II variant and the second immunomodulatory polypeptide may be covalently coupled, affinity coupled, or coupled as a fusion polypeptide.

In other embodiments, the composition can include one or more annexin-associated molecules such as, for example, the 11 kDa heterotetramer subunit, a heat shock protein (e.g., Hsp1, Hsp8, or Hsp9), or a non-protein that associates with annexin such as, for example, a phospholipid or a carbohydrate.

In some embodiments, the compositions described herein can optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, a composition as described herein can include a pharmaceutically acceptable carrier when the composition is used as described herein. A composition may be formulated in a pharmaceutical preparation in any one of a variety of forms adapted to the chosen route of administration, including routes suitable for stimulating an immune response to an antigen. Thus, a composition can be prepared for administration via known routes including, for example, oral; parenteral including intradermal, transcutaneous, subcutaneous, intramuscular, intravenous, intraperitoneal etc.; and/or topically, such as, intranasal, intrapulmonary, intramammary, intravaginal, intrauterine, intradermal, transcutaneous and/or rectal.

In some embodiments, the methods described herein can include administering sufficient annexin II variant to provide a dose of, for example, from about 100 ng/kg to about 50 mg/kg to the subject, although in some embodiments the methods may be performed by administering annexin II variant in a dose outside this range. In some of these embodiments, the method includes administering sufficient annexin II variant to provide a dose of from about 10 µg/kg to about 5 mg/kg to the subject, for example, a dose of from about 100 µg/kg to about 1 mg/kg or from about 50 µg/kg to about 500 µg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2$=(wt $kg^{0.425}$×height $cm^{0.725}$)×0.007184. In some embodiments, the methods may include administering sufficient annexin II variant to provide a dose of, for example, from about 0.01 mg/m$^2$ to about 10 mg/m$^2$.

In another aspect, this disclosure describes various methods for providing immunotherapy to a subject in need of such treatment. Generally, the methods involve administering an effective amount of a composition described herein to a subject in need of such treatment. As used herein, an effective amount refers to an amount, administered in an appropriate dose and regimen, to provide prophylactic or therapeutic immunotherapy. An effective amount can be any amount that reduces, limits the progression, ameliorates, or resolves, to any extent, the symptoms or clinical signs related to a condition compared to a similarly situated but untreated individual. "Ameliorate" refers to any reduction in the extent, severity, frequency, and/or likelihood of a symptom or clinical sign characteristic of a particular condition.

The compositions described herein provide a new strategy for providing immunotherapy that is applicable to immunotherapy directed against a wide array of conditions. As discussed above, such conditions can include tumors or conditions that result from infection by an infectious agent—immunotherapy in which a $T_h1$ immune response (i.e., a cell-mediated immune response) is desired. Accordingly, the methods also may be applicable for therapy directed against $T_h2$-mediated conditions such as, for example, allergy and/or asthma. In such cases, the compositions have utility because administering the compositions biases the immune system in favor of a $T_h1$/cell-mediated-dominant immune response and away from a $T_h2$ immune response.

In some embodiments, the methods can involve the preparation of a dendritic cell vaccine, which can then be administered to a subject in need of such treatment. The dendritic cells may be pulsed with an annexin II variant/antigen composition as described herein. Preparation of the dendritic cells in this manner may increase the cross presentation of antigen on MHC I and, therefore, the CD8+ T cell responses evoked by the dendritic cells of the vaccine.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

TABLE 1

Annexin II variants

| Designator | Amino Acid Sequence | SEQ ID NO |
|---|---|---|
| A-1 | ATVHEILCKL SLEGD | 12 |
| A-2 | SAVHEILCKL SLEGD | 13 |
| A-3 | STAHEILCKL SLEGD | 14 |
| A-4 | STVAEILCKL SLEGD | 15 |
| A-5 | STVHAILCKL SLEGD | 16 |
| A-6 | STVHEALCKL SLEGD | 17 |
| A-7 | STVHEIACKL SLEGD | 18 |
| A-8 | STVHEILAKL SLEGD | 19 |
| A-10 | STVHEILCKA SLEGD | 21 |
| A-11 | STVHEILCKL ALEGD | 22 |
| A-12 | STVHEILCKL SAEGD | 23 |
| A-13 | STVHEILCKL SLAGD | 24 |
| A-14 | STVHEILCKL SLEAD | 25 |
| A-15 | STVHEILCKL SLEGA | 26 |

Example 1

Bone marrow derived dendritic cells (BMDCs) were differentiated from C57BL/6 mice and pulsed with hgp100$_{25-33}$ (SEQ ID NO: 27) with annexin II-OVA fusion protein (SEQ ID NO:32) at equal concentration (*) or equal molecular ratio (**) as A2 monomer (SEQ ID NO:28) and incubated for 24 hours. Annexin A2 monomer was used as a positive control. Purified Pmel CD8+ T cells were added and co-cultured for an additional 48 hours. IFN-γ in the tissue culture supernatant was quantified by bead array. Results are shown in FIG. 1.

BMDCs were pulsed with OVA$_{248-274}$ (SEQ ID NO:31), annexin II (A2 monomer, SEQ ID NO:28), a combination of OVA$_{248-274}$ and annexin II (A2 monomer+OVA), or annexin II-OVA fusion protein (A2OVA, SEQ ID NO:32), and incubated for 24 hours. Purified OT-I CD8+ T cells were added and co-cultured for an additional 48 hours. IFN-γ in the tissue culture supernatant was quantified by bead array. Results are shown in FIG. 2.

BMDCs (wild-type, TLR4$^{-/-}$, and MyD88$^{-/-}$) were cultured with 20 ng/mL GM-CSF for six days, then pulsed with 50 ng Pam3CSK4, 50 ng LPS, or 50 μg of the N-terminal 15 amino acid annexin II fragment peptide (SEQ ID NO:5, A2-15aa). After 48 hours, cell culture supernatant was assayed for TNF by bead array. Results are shown in FIG. 10.

BDMCs (wild-type, TLR2$^{-/-}$, TLR4$^{-/-}$, and MyD88$^{-/-}$) were cultured with 20 ng/mL GM-CSF for six days, then pulsed with 50 ng Pam3CSK4, 50 ng LPS, 50 μg of the N-terminal 15 amino acid annexin II fragment peptide (SEQ ID NO:5, 15aa A2p), or 50 μg of annexin II variant A-6 (SEQ ID NO:17, 15aa A2p6 AL). After 48 hours, cells were stained for CD11c, MHC II, CD80, and CD86 and analyzed by flow cytometry. MFI shown is from a live cell, CD11c$^+$ MHCII$^+$ gate. Results gated for CD80 are shown in FIG. 11; results gated for CD86 are shown in FIG. 12.

Example 2

HEK 293 Blue Cells (Invivogen, San Diego, Calif.) stably transfected with hTLR2 were pulsed with annexin II-OVA fusion protein (A2OVA, SEQ ID NO:32) at equal concentration as annexin II monomer (A2 Peptide, SEQ ID NO:28). Scrambled annexin II N-terminus polypeptide (SEQ ID NO:29, Scrambled) and an annexin II fragment (SEQ ID NO:30, Minus p11) were used as controls. Cells were incubated for 48 hours. Following incubation, supernatant was added to Quanti-Blue (Invivogen, San Diego, Calif.) for secreted alkaline phosphatase detection. Results are shown in FIG. 3.

Example 3

Figure 4A:
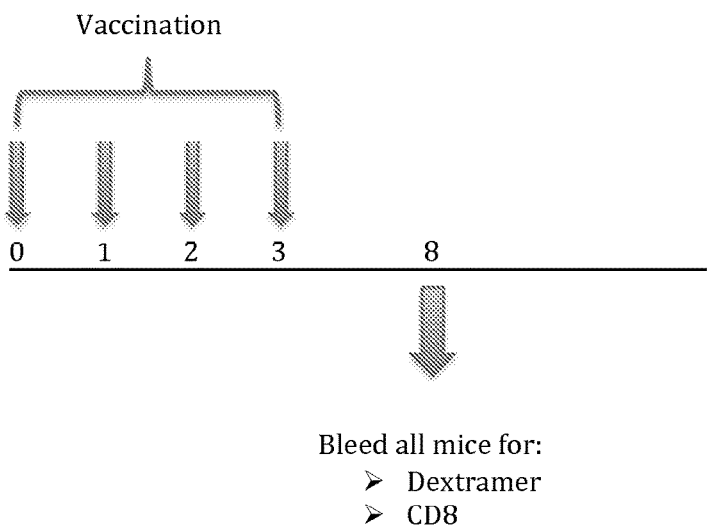
FIG. 4. (A) Experimental protocol; (B) Data demonstrating activity of annexin II-OVA fusion protein in vivo.
Figure 4B:
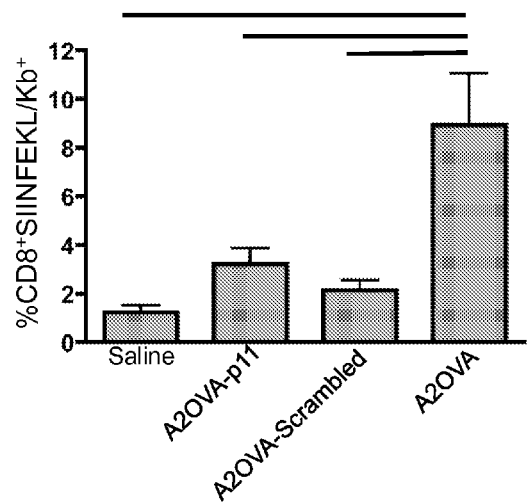

As shown in FIG. 4A, BL/6 mice were vaccinated for four consecutive days in the hind leg with Poly:ICLC and 50 μg of A2OVA fusion protein (SEQ ID NO:32), A2OVA-pp11 (SEQ ID NO:30, or scrambled A2OVA peptide (SEQ ID NO:29). On Day 8, mice were bled and whole blood was analyzed for CD8$^+$SIINFEKL$^+$ expansion. Results are shown in FIG. 4B.

Figure 8:
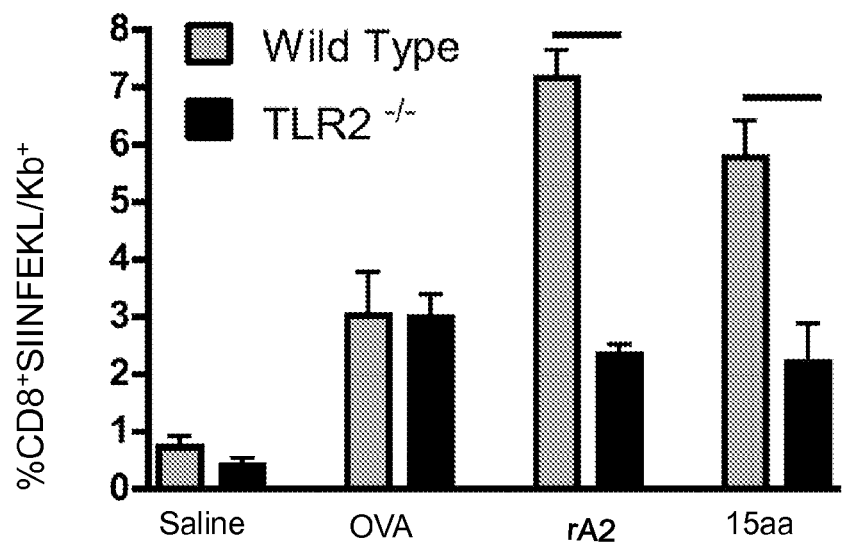
FIG. 8. Data comparing in vivo annexin II activity of full length annexin II and the 15 amino acid N-terminal annexin II fragment.

Separately, BL/6 mice were vaccinated for four consecutive days in the hind leg with ovalbumin (OVA), ovalbumin+ 50 μg of the N-terminal 15 amino acid annexin II fragment peptide (SEQ ID NO:5, 15aa), or ovalbumin+50 μg annexin II (SEQ ID NO:28, rA2). On Day 8, mice were bled and whole blood was analyzed for CD8+SIINFEKL+ expansion. Results are shown in FIG. 8.

BL/6 mice also were vaccinated for four consecutive days in the hind leg with ovalbumin (OVA), ovalbumin+ and 50 µg of the N-terminal 15 amino acid annexin II fragment peptide (SEQ ID NO:5, 15aa), or ovalbumin+50 µg the annexin II variant A-6 (Table 1, SEQ ID NO:17, 15aaP6). On Day 8, mice were bled and whole blood was analyzed for CD8+SIINFEKL+ expansion. Results are shown in FIG. 9.

Example 4

Figure 5A:
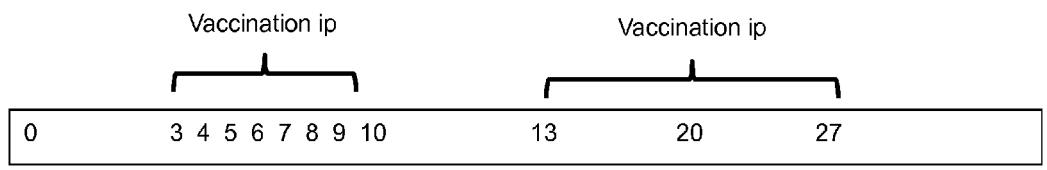
FIG. 5. (A) Experimental protocol; (B) Data demonstrating activity of annexin II-OVA fusion protein in reducing tumor size in vivo; (C) Data demonstrating activity of annexin II-OVA fusion protein in increasing survival.
Figure 5C:
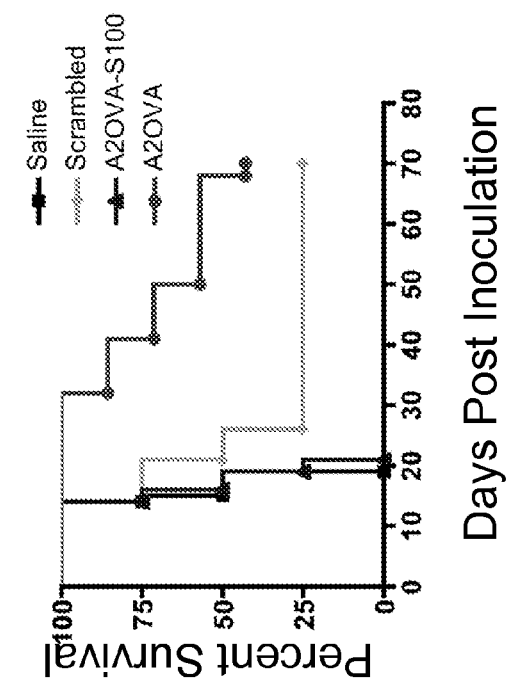
Figure 5B:
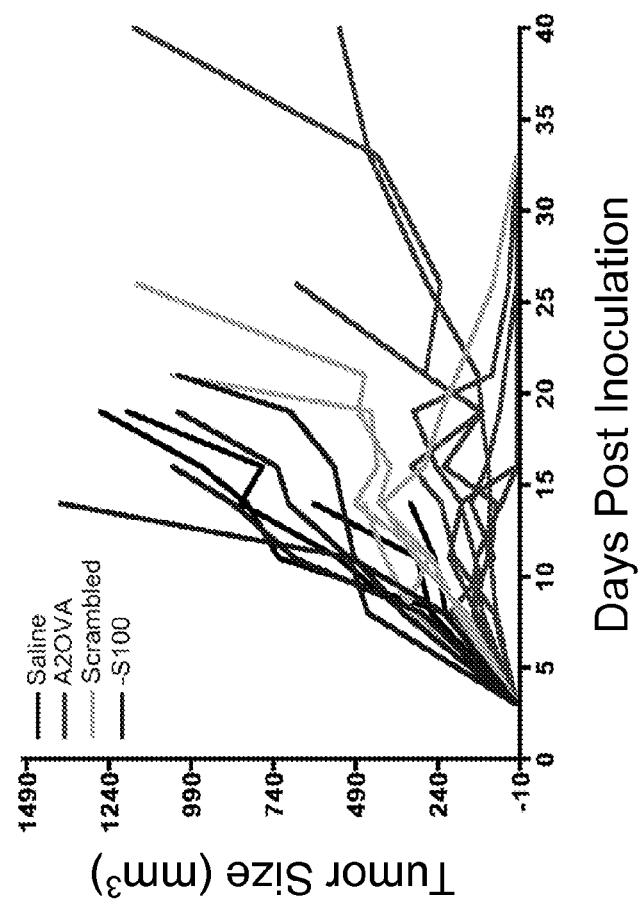

As shown in FIG. 5A, breast-tumor-bearing mice were vaccinated for 10 consecutive days intraperitoneally with A2OVA fusion protein (SEQ ID NO:32), A2OVA-S100 (SEQ ID NO:33, or scrambled A2OVA peptide (SEQ ID NO:29). Tumors were measured for growth and mice were followed for survival. Mice were sacrificed when tumor reached 1000 mm³. Results are shown in FIG. 5B.

Example 5

TLR2-transfected HEK 293 Blue Cells and TLR4-transfected HEK 293 Blue Cells (Invivogen, San Diego, Calif.) were pulsed with the N-terminal 15 amino acid annexin II fragment peptide (15aa Peptide, SEQ ID NO:5) at different concentrations. Cells were incubated for 48 hours. Following incubation, supernatant was added to Quanti-Blue (Invivogen, San Diego, Calif.) for secreted alkaline phosphatase detection. Results are shown in FIG. 6.

TLR2-transfected HEK 293 Blue Cells and TLR4-transfected HEK 293 Blue Cells (Invivogen, San Diego, Calif.) were pulsed with the N-terminal 15 amino acid annexin II fragment peptide (15aa Peptide, SEQ ID NO:5) or one of the annexin II variants shown in Table 1. Cells were incubated for 48 hours. Following incubation, supernatant was added to Quanti-Blue (Invivogen, San Diego, Calif.) for secreted alkaline phosphatase detection.

Example 6

Preparation of Annexin II Variant Fusion Peptides

Annexin II variant fusion peptides are generated as described in Li et al., 2003 *J. Immunother.* 26:320-331.

Briefly, an annexin II polynucleotide (e.g., a polynucleotide that encodes a polypeptide having the amino acid sequence of any one of SEQ ID NO:1-6, 11-24) is genetically linked, using standard recombination techniques, to fusion partner TNT. TNT is an antibody that targets tumors by binding to DNA exposed in necrotic zones.

Construction and expression of the fusion peptide is performed using a commercially available cloning kit and expression plasmids (Glutamine Synthetase Gene Amplification System, Lonza Biologics, Inc., Slough, UK). A plasmid carrying the gene encoding the light chain of TNT and a separate plasmid carrying the gene encoding the heavy of TNT are prepared. The annexin II variant polynucleotide is inserted into the N-terminus of the TNT heavy chain gene under the control of an antibody leader sequence using standard recombination techniques. This TNThc-A2 fusion gene is inserted into a commercially available expression vector.

The expression vector containing the TNThc-A2 fusion gene and the plasmid carrying the gene encoding the light chain of TNT are co-transfected into cells according to instructions provided by the expression system manufacturer. Cell culture media is changed weekly following transfection for three weeks. Clones best expressing the TNT-A2 fusion peptide are chosen by using a protein identification assay (e.g., ELISA) on the culture supernatant and are used to produce large quantities of the TNT-A2 fusion peptide as described in Li et al., 2003 *J. Immunother.* 26:320-331.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

```
SEQ ID NO: 1 (35aa)
STVHEILCKL SLEGDHSTPP SAYGSVKPYT NFDAE

SEQ ID NO: 2 (30aa)
STVHEILCKL SLEGDHSTPP SAYGSVKPYT

SEQ ID NO: 3 (25aa)
STVHEILCKL SLEGDHSTPP SAYGS

SEQ ID NO: 4 (20aa)
STVHEILCKL SLEGDHSTPP

SEQ ID NO: 5 (15aa)
STVHEILCKL SLEGD

SEQ ID NO: 6 (10aa)
STVHEILCKL
```

SEQ ID NO: 7 (15aaOVA, Ahx = 6-aminohexanoic acid)
STVHEILCKL SLEGD(Ahx)EQLE SIINFEKLTE WT SEQ ID NO: 8 (15aaP6OVA, Ahx =6-aminohexanoic acid)
STVHEALCKL SLEGD(Ahx)EQLE SIINFEKLTE WT

SEQ ID NO: 9 (OVA)
EQLESIINFE KLTEWT

SEQ ID NO: 10 (NXX-Ahx-XXN, Ahx = 6-aminohexanoic acid):
STVHEILCKL SLEGD(Ahx)DGEL SLKCLIEHVT S SEQ ID NO: 11 (CXX-Ahx-XXC, Ahx = 6-aminohexanoic acid)
DGELSLKCLI EHVTS(Ahx)STVH EILCKLSLEG D

SEQ ID NO: 12 (A-1)
ATVHEILCKL SLEGD

SEQ ID NO: 13 (A-2)
SAVHEILCKL SLEGD

SEQ ID NO: 14 (A-3)
STAHEILCKL SLEGD

SEQ ID NO: 15 (A-4)
STVAEILCKL SLEGD

SEQ ID NO: 16 (A-5)
STVHAILCKL SLEGD

SEQ ID NO: 17 (A-6)
STVHEALCKL SLEGD

SEQ ID NO: 18 (A-7)
STVHEIACKL SLEGD

SEQ ID NO: 19 (A-8)
STVHEILAKL SLEGD

SEQ ID NO: 20 (A-9)
STVHEILCAL SLEGD

SEQ ID NO: 21 (A-10)
STVHEILCKA SLEGD

SEQ ID NO: 22 (A-11)
STVHEILCKL ALEGD

SEQ ID NO: 23 (A-12)
STVHEILCKL SAEGD

SEQ ID NO: 24 (A-13)
STVHEILCKL SLAGD

SEQ ID NO: 25 (A-14)
STVHEILCKL SLEAD

SEQ ID NO: 26 (A-15)
STVHEILCKL SLEGA

SEQ ID NO: 27 (hgp100$_{25-33}$)
KVPRNQDWL

SEQ ID NO: 28 (rA2)
MSTVHEILCK LSLEGDHSTP PSAYGSVKAY TNFDAERDAL

NIETAIKTKG VDEVTIVNIL TNRSNAQRQD IAFAYQRRTK

KELASALKSA LSGHLETVIL GLLKTPAQYD ASELKASMKG

LGTDEDSLIE IICSRTNQEL QEINRVYKEM YKTDLEKDII

SDTSGDFRKL MVALAKGRRA EDGSVIDYEL IDQDARDLYD

AGVKRKGTDV PKWISIMTER SVPHLQKVFD RYKSYSPYDM

LESIRKEVKG DLENAFLNLV QCIQNKPLYF ADRLYDSMKG

KGTRDKVLIR IMVSRSEVDM LKIRSEFKRK YGKSLYYYIQ

QDTKGDYQKA LLYLCGGDD

SEQ ID NO: 29 (Scrambled)
GSCTESIEAL HVLELVSPYT KSHNTPDSKG DYPFAEQLES

IINFEKLTEW T

SEQ ID NO: 30 (A2OVA-pp11)
DHSTPPSAYG SVKPYTNFDA EEQLESIINF EKLTEWT

SEQ ID NO: 31 (OVA$_{248-274}$)
EVSQLEQLES IINFEKLTEE WTSSNVM

SEQ ID NO: 32 (annexin II-OVA fusion protein)
STVHEILCKL SLEGDHSTPP SAYGSVKPYT NFDAEEQLES

IINFEKLTEW T

---

What is claimed is:

1. A composition comprising an immunomodulatory annexin II variant comprising:
 a domain corresponding to amino acids 1-15 of SEQ ID NO:1, the domain comprising:
  at least one amino acid substitution compared to amino acids 1-15 of SEQ ID NO:1; and
  no more than two amino acid substitutions compared to amino acids 1-15 of SEQ ID NO:1.

2. The composition of claim 1 further comprising at least one antigen.

3. The composition of claim 1 further comprising a second immunomodulatory component, the second immunomodulatory component comprising an adjuvant.

4. The composition of claim 2, wherein the antigen is coupled to the annexin II variant.

5. The composition of claim 1 further comprising a targeting moiety coupled to the annexin II variant.

6. The composition of claim 1 further comprising a stabilizing moiety coupled to the annexin II variant.

7. The composition of claim 4, wherein the coupling comprises a covalent coupling.

8. The composition of claim 7, wherein the covalent coupling comprises a covalent crosslink between the at least one annexin II variant and the antigen.

9. The composition of claim 7, wherein the covalent coupling comprises a polypeptide fusion between the at least one annexin II variant and the antigen.

10. The composition of claim 4, wherein the coupling comprises an affinity coupling.

11. The composition of claim 3 wherein the second immunomodulatory component is coupled to the annexin II variant.

12. The composition of claim 5 wherein the coupling comprises a covalent coupling.

13. The composition of claim 5 wherein the coupling comprises an affinity coupling.

14. The composition of claim 6 wherein the coupling comprises a covalent coupling.

15. The composition of claim 6 wherein the coupling comprises an affinity coupling.

16. The composition of claim 1 farther comprising a pharmaceutically acceptable carrier.

17. A method comprising:
   administering to a subject in need of such treatment an effective amount of a composition comprising an annexin II variant, the annexin II variant comprising:
   a domain corresponding to amino acids 1-15 of SEQ ID NO:1, the domain comprising:
      at least one amino acid substitution compared to amino acids 1-15 of SEQ ID NO:1; and
      no more than two amino acid substitutions compared to amino acids 1-15 of SEQ ID NO:1.

18. A method comprising:
   contacting dendritic cells with a composition comprising:
      an annexin II variant comprising:
         a domain corresponding to amino acids 1-15 of SEQ ID NO:1, the domain comprising:
            at least one amino acid substitution compared to amino acids 1-15 of SEQ ID NO:1; and
            no more than two amino acid substitutions compared to amino acids 1-15 of SEQ ID NO:1; and
      an antigen.

19. The method of claim 18 further comprising administering the dendritic cells to a subject.

* * * * *

SEQUENCE LISTING

<160> NUMBER OF SEQ ID NOS: 32

<210> SEQ ID NO 1
<211> LENGTH: 35
<212> TYPE: PRT
<213> ORGANISM: artificial
<220> FEATURE:
<223> OTHER INFORMATION: annexin II variant polypeptide

<400> SEQUENCE: 1

Ser Thr Val His Glu Ile Leu Cys Lys Leu Ser Leu Glu Gly Asp His
1               5                   10                  15

Ser Thr Pro Pro Ser Ala Tyr Gly Ser Val Lys Pro Tyr Thr Asn Phe
            20                  25                  30

Asp Ala Glu
        35

-continued

```
<210> SEQ ID NO 2
<211> LENGTH: 30
<212> TYPE: PRT
<213> ORGANISM: artificial
<220> FEATURE:
<223> OTHER INFORMATION: annexin II variant polypeptide

<400> SEQUENCE: 2

Ser Thr Val His Glu Ile Leu Cys Lys Leu Ser Leu Glu Gly Asp His
1               5                   10                  15

Ser Thr Pro Pro Ser Ala Tyr Gly Ser Val Lys Pro Tyr Thr
            20                  25                  30

<210> SEQ ID NO 3
<211> LENGTH: 25
<212> TYPE: PRT
<213> ORGANISM: artificial
<220> FEATURE:
<223> OTHER INFORMATION: annexin II variant polypeptide

<400> SEQUENCE: 3

Ser Thr Val His Glu Ile Leu Cys Lys Leu Ser Leu Glu Gly Asp His
1               5                   10                  15

Ser Thr Pro Pro Ser Ala Tyr Gly Ser
            20                  25

<210> SEQ ID NO 4
<211> LENGTH: 20
<212> TYPE: PRT
<213> ORGANISM: artificial
<220> FEATURE:
<223> OTHER INFORMATION: annexin II variant polypeptide

<400> SEQUENCE: 4

Ser Thr Val His Glu Ile Leu Cys Lys Leu Ser Leu Glu Gly Asp His
1               5                   10                  15

Ser Thr Pro Pro
            20

<210> SEQ ID NO 5
<211> LENGTH: 15
<212> TYPE: PRT
<213> ORGANISM: artificial
<220> FEATURE:
<223> OTHER INFORMATION: annexin II variant polypeptide

<400> SEQUENCE: 5

Ser Thr Val His Glu Ile Leu Cys Lys Leu Ser Leu Glu Gly Asp
1               5                   10                  15

<210> SEQ ID NO 6
<211> LENGTH: 10
<212> TYPE: PRT
<213> ORGANISM: artificial
<220> FEATURE:
<223> OTHER INFORMATION: annexin II variant polypeptide

<400> SEQUENCE: 6

Ser Thr Val His Glu Ile Leu Cys Lys Leu
1               5                   10

<210> SEQ ID NO 7
<211> LENGTH: 32
<212> TYPE: PRT
<213> ORGANISM: artificial
```

```
<220> FEATURE:
<223> OTHER INFORMATION: OVA polypeptide
<220> FEATURE:
<221> NAME/KEY: MISC_FEATURE
<222> LOCATION: (16)..(16)
<223> OTHER INFORMATION: X at position 16 is 6-aminohexanoic acid

<400> SEQUENCE: 7

Ser Thr Val His Glu Ile Leu Cys Lys Leu Ser Leu Glu Gly Asp Xaa
1               5                   10                  15

Glu Gln Leu Glu Ser Ile Ile Asn Phe Glu Lys Leu Thr Glu Trp Thr
            20                  25                  30

<210> SEQ ID NO 8
<211> LENGTH: 32
<212> TYPE: PRT
<213> ORGANISM: artificial
<220> FEATURE:
<223> OTHER INFORMATION: OVA polypeptide
<220> FEATURE:
<221> NAME/KEY: MISC_FEATURE
<222> LOCATION: (16)..(16)
<223> OTHER INFORMATION: X at position 16 is 6-aminohexanoic acid

<400> SEQUENCE: 8

Ser Thr Val His Glu Ala Leu Cys Lys Leu Ser Leu Glu Gly Asp Xaa
1               5                   10                  15

Glu Gln Leu Glu Ser Ile Ile Asn Phe Glu Lys Leu Thr Glu Trp Thr
            20                  25                  30

<210> SEQ ID NO 9
<211> LENGTH: 16
<212> TYPE: PRT
<213> ORGANISM: artificial
<220> FEATURE:
<223> OTHER INFORMATION: OVA polypeptide

<400> SEQUENCE: 9

Glu Gln Leu Glu Ser Ile Ile Asn Phe Glu Lys Leu Thr Glu Trp Thr
1               5                   10                  15

<210> SEQ ID NO 10
<211> LENGTH: 31
<212> TYPE: PRT
<213> ORGANISM: artificial
<220> FEATURE:
<223> OTHER INFORMATION: palindrome of annexin II variant polypeptide
<220> FEATURE:
<221> NAME/KEY: MISC_FEATURE
<222> LOCATION: (16)..(16)
<223> OTHER INFORMATION: X at position 16 is 6-aminohexanoic acid

<400> SEQUENCE: 10

Ser Thr Val His Glu Ile Leu Cys Lys Leu Ser Leu Glu Gly Asp Xaa
1               5                   10                  15

Asp Gly Glu Leu Ser Leu Lys Cys Leu Ile Glu His Val Thr Ser
            20                  25                  30

<210> SEQ ID NO 11
<211> LENGTH: 31
<212> TYPE: PRT
<213> ORGANISM: artificial
<220> FEATURE:
<223> OTHER INFORMATION: palindrome of annexin II variant polypeptide
<220> FEATURE:
<221> NAME/KEY: MISC_FEATURE
<222> LOCATION: (16)..(16)
<223> OTHER INFORMATION: X at position 16 is 6-aminohexanoic acid
```

```
<400> SEQUENCE: 11

Asp Gly Glu Leu Ser Leu Lys Cys Leu Ile Glu His Val Thr Ser Xaa
1               5                   10                  15

Ser Thr Val His Glu Ile Leu Cys Lys Leu Ser Leu Glu Gly Asp
                20                  25                  30

<210> SEQ ID NO 12
<211> LENGTH: 15
<212> TYPE: PRT
<213> ORGANISM: artificial
<220> FEATURE:
<223> OTHER INFORMATION: annexin II variant polypeptide

<400> SEQUENCE: 12

Ala Thr Val His Glu Ile Leu Cys Lys Leu Ser Leu Glu Gly Asp
1               5                   10                  15

<210> SEQ ID NO 13
<211> LENGTH: 15
<212> TYPE: PRT
<213> ORGANISM: artificial
<220> FEATURE:
<223> OTHER INFORMATION: annexin II variant polypeptide

<400> SEQUENCE: 13

Ser Ala Val His Glu Ile Leu Cys Lys Leu Ser Leu Glu Gly Asp
1               5                   10                  15

<210> SEQ ID NO 14
<211> LENGTH: 15
<212> TYPE: PRT
<213> ORGANISM: artificial
<220> FEATURE:
<223> OTHER INFORMATION: annexin II variant polypeptide

<400> SEQUENCE: 14

Ser Thr Ala His Glu Ile Leu Cys Lys Leu Ser Leu Glu Gly Asp
1               5                   10                  15

<210> SEQ ID NO 15
<211> LENGTH: 15
<212> TYPE: PRT
<213> ORGANISM: artificial
<220> FEATURE:
<223> OTHER INFORMATION: annexin II variant polypeptide

<400> SEQUENCE: 15

Ser Thr Val Ala Glu Ile Leu Cys Lys Leu Ser Leu Glu Gly Asp
1               5                   10                  15

<210> SEQ ID NO 16
<211> LENGTH: 15
<212> TYPE: PRT
<213> ORGANISM: artificial
<220> FEATURE:
<223> OTHER INFORMATION: annexin II variant polypeptide

<400> SEQUENCE: 16

Ser Thr Val His Ala Ile Leu Cys Lys Leu Ser Leu Glu Gly Asp
1               5                   10                  15

<210> SEQ ID NO 17
<211> LENGTH: 15
<212> TYPE: PRT
<213> ORGANISM: artificial
```

```
<220> FEATURE:
<223> OTHER INFORMATION: annexin II variant polypeptide

<400> SEQUENCE: 17

Ser Thr Val His Glu Ala Leu Cys Lys Leu Ser Leu Glu Gly Asp
1               5                   10                  15

<210> SEQ ID NO 18
<211> LENGTH: 15
<212> TYPE: PRT
<213> ORGANISM: artificial
<220> FEATURE:
<223> OTHER INFORMATION: annexin II variant polypeptide

<400> SEQUENCE: 18

Ser Thr Val His Glu Ile Ala Cys Lys Leu Ser Leu Glu Gly Asp
1               5                   10                  15

<210> SEQ ID NO 19
<211> LENGTH: 15
<212> TYPE: PRT
<213> ORGANISM: artificial
<220> FEATURE:
<223> OTHER INFORMATION: annexin II variant polypeptide

<400> SEQUENCE: 19

Ser Thr Val His Glu Ile Leu Ala Lys Leu Ser Leu Glu Gly Asp
1               5                   10                  15

<210> SEQ ID NO 20
<211> LENGTH: 15
<212> TYPE: PRT
<213> ORGANISM: artificial
<220> FEATURE:
<223> OTHER INFORMATION: annexin II variant polypeptide

<400> SEQUENCE: 20

Ser Thr Val His Glu Ile Leu Cys Ala Leu Ser Leu Glu Gly Asp
1               5                   10                  15

<210> SEQ ID NO 21
<211> LENGTH: 15
<212> TYPE: PRT
<213> ORGANISM: artificial
<220> FEATURE:
<223> OTHER INFORMATION: annexin II variant polypeptide

<400> SEQUENCE: 21

Ser Thr Val His Glu Ile Leu Cys Lys Ala Ser Leu Glu Gly Asp
1               5                   10                  15

<210> SEQ ID NO 22
<211> LENGTH: 15
<212> TYPE: PRT
<213> ORGANISM: artificial
<220> FEATURE:
<223> OTHER INFORMATION: annexin II variant polypeptide

<400> SEQUENCE: 22

Ser Thr Val His Glu Ile Leu Cys Lys Leu Ala Leu Glu Gly Asp
1               5                   10                  15

<210> SEQ ID NO 23
<211> LENGTH: 15
<212> TYPE: PRT
<213> ORGANISM: artificial
```

```
<220> FEATURE:
<223> OTHER INFORMATION: annexin II variant polypeptide

<400> SEQUENCE: 23

Ser Thr Val His Glu Ile Leu Cys Lys Leu Ser Ala Glu Gly Asp
1               5                   10                  15

<210> SEQ ID NO 24
<211> LENGTH: 15
<212> TYPE: PRT
<213> ORGANISM: artificial
<220> FEATURE:
<223> OTHER INFORMATION: annexin II variant polypeptide

<400> SEQUENCE: 24

Ser Thr Val His Glu Ile Leu Cys Lys Leu Ser Leu Ala Gly Asp
1               5                   10                  15

<210> SEQ ID NO 25
<211> LENGTH: 15
<212> TYPE: PRT
<213> ORGANISM: artificial
<220> FEATURE:
<223> OTHER INFORMATION: annexin II variant polypeptide

<400> SEQUENCE: 25

Ser Thr Val His Glu Ile Leu Cys Lys Leu Ser Leu Glu Ala Asp
1               5                   10                  15

<210> SEQ ID NO 26
<211> LENGTH: 15
<212> TYPE: PRT
<213> ORGANISM: artificial
<220> FEATURE:
<223> OTHER INFORMATION: annexin II variant polypeptide

<400> SEQUENCE: 26

Ser Thr Val His Glu Ile Leu Cys Lys Leu Ser Leu Glu Gly Ala
1               5                   10                  15

<210> SEQ ID NO 27
<211> LENGTH: 9
<212> TYPE: PRT
<213> ORGANISM: artificial
<220> FEATURE:
<223> OTHER INFORMATION: hgp100[25-33] polypeptide

<400> SEQUENCE: 27

Lys Val Pro Arg Asn Gln Asp Trp Leu
1               5

<210> SEQ ID NO 28
<211> LENGTH: 339
<212> TYPE: PRT
<213> ORGANISM: artificial
<220> FEATURE:
<223> OTHER INFORMATION: annexin A2 monomer polypeptide

<400> SEQUENCE: 28

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45
```

Lys Gly Val Asp Glu Val Thr Ile Val Asn Ile Leu Thr Asn Arg Ser
 50                  55                  60

Asn Ala Gln Arg Gln Asp Ile Ala Phe Ala Tyr Gln Arg Arg Thr Lys
 65                  70                  75                  80

Lys Glu Leu Ala Ser Ala Leu Lys Ser Ala Leu Ser Gly His Leu Glu
                 85                  90                  95

Thr Val Ile Leu Gly Leu Leu Lys Thr Pro Ala Gln Tyr Asp Ala Ser
                100                 105                 110

Glu Leu Lys Ala Ser Met Lys Gly Leu Gly Thr Asp Glu Asp Ser Leu
            115                 120                 125

Ile Glu Ile Ile Cys Ser Arg Thr Asn Gln Glu Leu Gln Glu Ile Asn
130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 29
<211> LENGTH: 51
<212> TYPE: PRT
<213> ORGANISM: artificial
<220> FEATURE:
<223> OTHER INFORMATION: scrambled annexin II N-terminus polypeptide

<400> SEQUENCE: 29

Gly Ser Cys Thr Glu Ser Ile Glu Ala Leu His Val Leu Glu Leu Val
1               5                   10                  15

Ser Pro Tyr Thr Lys Ser His Asn Thr Pro Asp Ser Lys Gly Asp Tyr
                20                  25                  30

Pro Phe Ala Glu Gln Leu Glu Ser Ile Ile Asn Phe Glu Lys Leu Thr
            35                  40                  45

Glu Trp Thr
    50

```
<210> SEQ ID NO 30
<211> LENGTH: 37
<212> TYPE: PRT
<213> ORGANISM: artificial
<220> FEATURE:
<223> OTHER INFORMATION: annexin II peptide fragment minus p11

<400> SEQUENCE: 30

Asp His Ser Thr Pro Pro Ser Ala Tyr Gly Ser Val Lys Pro Tyr Thr
1               5                   10                  15

Asn Phe Asp Ala Glu Glu Gln Leu Glu Ser Ile Ile Asn Phe Glu Lys
                20                  25                  30

Leu Thr Glu Trp Thr
        35

<210> SEQ ID NO 31
<211> LENGTH: 27
<212> TYPE: PRT
<213> ORGANISM: artificial
<220> FEATURE:
<223> OTHER INFORMATION: OVA[248-274] polypeptide

<400> SEQUENCE: 31

Glu Val Ser Gln Leu Glu Gln Leu Glu Ser Ile Ile Asn Phe Glu Lys
1               5                   10                  15

Leu Thr Glu Glu Trp Thr Ser Ser Asn Val Met
                20                  25

<210> SEQ ID NO 32
<211> LENGTH: 51
<212> TYPE: PRT
<213> ORGANISM: artificial
<220> FEATURE:
<223> OTHER INFORMATION: annexin II-OVA fusion protein (A2OVA)
      polypeptide

<400> SEQUENCE: 32

Ser Thr Val His Glu Ile Leu Cys Lys Leu Ser Leu Glu Gly Asp His
1               5                   10                  15

Ser Thr Pro Pro Ser Ala Tyr Gly Ser Val Lys Pro Tyr Thr Asn Phe
                20                  25                  30

Asp Ala Glu Glu Gln Leu Glu Ser Ile Ile Asn Phe Glu Lys Leu Thr
        35                  40                  45

Glu Trp Thr
    50
```